United States Patent
Hartley et al.

(10) Patent No.: US 12,023,135 B2
(45) Date of Patent: Jul. 2, 2024

(54) CARDIOPULMONARY HEALTH MONITORING USING THERMAL CAMERA AND AUDIO SENSOR

(71) Applicant: Roc8Sci Co., Arcadia, CA (US)

(72) Inventors: Frank Thomas Hartley, Arcadia, CA (US); Charles Henry Ross, Urbana, IL (US)

(73) Assignee: Roc8Sci Co., Arcadia, CA (US)

( * ) Notice: Subject to any disclaimer, the term of this patent is extended or adjusted under 35 U.S.C. 154(b) by 0 days.

(21) Appl. No.: 18/527,127

(22) Filed: Dec. 1, 2023

(65) Prior Publication Data

US 2024/0090778 A1 Mar. 21, 2024

Related U.S. Application Data

(63) Continuation of application No. 17/510,357, filed on Oct. 25, 2021.
(Continued)

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0077* (2013.01); *A61B 5/015* (2013.01);
(Continued)

(58) Field of Classification Search
None
See application file for complete search history.

(56) References Cited

U.S. PATENT DOCUMENTS

| | | |
|---|---|---|
| 2007/0118054 A1 | 5/2007 | Pinhas et al. |
| 2008/0045847 A1 | 2/2008 | Farag et al. |

(Continued)

FOREIGN PATENT DOCUMENTS

| | | |
|---|---|---|
| WO | WO-2018/212710 | 11/2018 |
| WO | WO-2019/162459 | 8/2019 |

OTHER PUBLICATIONS

Alex Davies; "Heat-Seeking Cameras Could Help Keep Self-Driving Cars Safe;" Wired.com; Apr. 21, 2018; 5 pages.
(Continued)

*Primary Examiner* — Yi-Shan Yang
(74) *Attorney, Agent, or Firm* — FOLEY & LARDNER LLP

(57) ABSTRACT

System and method for monitoring vital signs of a subject, such as a sleeping patient. A health monitoring device includes a thermal camera such as an uncooled microbolometer array, to monitor breathing, pulse, core temperature, and other vital signs. An audio sensor, e.g., microphone, may be used for monitoring patient respiratory sounds and other sounds. Further information such as pulse rate, PRV, blood pressure, breathing rate and oxygenation level are derived from these signals. The health monitoring device utilizes acquired signals and higher order data in analyzing patient conditions and behaviors. Higher order data include visual data based upon thermal camera signals and audio data based upon audio sensor signals. A processor is configured to output a health determination relating to one or more health parameters of the patient by inputting one or both of the visual data and the audio data into one or more machine learning models.

19 Claims, 12 Drawing Sheets

Related U.S. Application Data

(60) Provisional application No. 63/107,036, filed on Oct. 29, 2020.

(51) Int. Cl.
    *A61B 5/01*     (2006.01)
    *A61B 7/00*     (2006.01)

(52) U.S. Cl.
    CPC .......... *A61B 5/7264* (2013.01); *A61B 5/7267* (2013.01); *A61B 5/742* (2013.01); *A61B 5/746* (2013.01); *A61B 7/003* (2013.01)

(56) References Cited

U.S. PATENT DOCUMENTS

| | | | |
|---|---|---|---|
| 2008/0161661 A1* | 7/2008 | Gizewski | A61B 5/0064 600/306 |
| 2011/0112442 A1 | 5/2011 | Meger | |
| 2012/0075463 A1* | 3/2012 | Chen | G01S 11/12 348/E5.09 |
| 2012/0289850 A1 | 11/2012 | Xu et al. | |
| 2014/0152424 A1 | 6/2014 | Steven et al. | |
| 2016/0278641 A1 | 9/2016 | Venkataramani | |
| 2016/0300364 A1 | 10/2016 | Abreo | |
| 2018/0049669 A1 | 2/2018 | Vu et al. | |
| 2018/0052971 A1 | 2/2018 | Hanina et al. | |
| 2018/0055384 A1 | 3/2018 | Ambili et al. | |
| 2018/0199870 A1 | 7/2018 | Lee et al. | |
| 2019/0083031 A1 | 3/2019 | Hanina et al. | |
| 2019/0115093 A1 | 4/2019 | Firoozabadi et al. | |
| 2019/0385711 A1 | 12/2019 | Shriberg et al. | |
| 2020/0178840 A1 | 6/2020 | Yeh et al. | |
| 2021/0177343 A1 | 6/2021 | Zhong et al. | |
| 2022/0047160 A1 | 2/2022 | Yoo | |

OTHER PUBLICATIONS

Ali I. Siam et al., "Efficient video-based breathing pattern and respiration rate monitoring for remote health monitoring," J. Opt. Soc. Am. A 37, C118-C124 (2020), Published: Aug. 31, 2020, https://doi.org/10.1364/JOSAA.399284, viewed on Jan. 27, 2023.

Amazon, Factorization Machines, https ://web .archive .org/web/20180731163 758/https ://docs .aws.amazon .com/sagemaker/latest/dg/fact-machines.html, Jul. 31, 2018, viewed on Apr. 1, 2022.

Automatic Layerwise Acquisition of Thermal and Geometric Data of the Electron Beam Melting Process Using Infrared Thermography Ridwan, S., Mireles, J., Gaytan, S.M., Espalin, D., Wicker, R.B. W.M. Keck Center for 3D Innovation, The University of Texas at El Paso, El Paso, Texas.

Belle et al., "A Continuous Real-Time Analytic for Predicting Instability in Acute Care Rapid Response Team Activations," World Academy of Science, Engineering and Technology International Journal of Medical and Health Sciences vol. 14, No. 11, Dec. 2020, 8 pages.

Carina Pereira et al. Remote monitoring of breathing dynamics using infrared thermography. Biomed Opt Express. Oct. 16, 2015;6(V 11 ):4378-94. doi: 10.1364/BOE.6.004378. PM ID: 26601003; PMCID: PMC4646547. viewed on Feb. 3, 2022.

Carina Pereira et al., "Noncontact Monitoring of Respiratory Rate in Newborn Infants Using Thermal Imaging," in IEEE Transactions on Biomedical Engineering, vol. 66, No. 4, pp. 1105-1114, Apr. 2019, doi: 10.1109/TBME.2018.2866878, viewed on Jan. 27, 2023.

Carlos Granda; "As businesses reopen, some look to thermal camera that can read body temperatures;" abc7.com Los Angeles; https://abc7.com/thermal-camera-seek-reading-temperature-symptoms-of-covid-19/6173237/; May 11, 2020; 3 pages.

Cheng Yang et al., "Sleep Apnea Detection via Depth Video and Audio Feature Learning," in IEEE Transactions on Multimedia, vol. 19, No. 4, pp. 822-835, Apr. 2017, doi: 10.1109/TMM.2016.2626969, viewed on Apr. 1, 2022.

Ching Wang et al., "Unconstrained Video Monitoring of Breathing Behavior and Application to Diagnosis of Sleep Apnea," in IEEE Transactions on Biomedical Engineering, vol. 61, No. 2, pp. 396-404, Feb. 2014, doi: 10.1109/TBME.2013.2280132. viewed on Feb. 3, 2023.

Christian Hessler et al., "A Non-contact Method for Extracting Heart and Respiration Rates," 2020 17th Conference on Computer and Robot Vision (CRV), Ottawa, ON, Canada, 2020, pp. 1-8, doi: 10.1109/CRV50864.2020.00009. viewed on Feb. 3, 2022.

Eggenberger et al., "Prediction of Core Body Temperature Based on Skin Temperature, Heat Flux, and Heart Rate Under Different Exercise and Clothing Conditions in the Heat in Young Adult Males," Front. Physiol., https://doi.org/10.3389/fphys.2018.01780, Dec. 10, 2018; 11 pages.

Final Office Action on U.S. Appl. No. 17/510,357 dated Aug. 12, 2022 (43 pages).

Flir, How Do Thermal Cameras Work?, https://www.flir.com/discover/rd-science/how-do-thermal-cameras-work/, Jun. 16, 2020, viewed on Aug. 1, 2022.

Fluke, How infrared cameras work, https://www.fluke.com/en-us/learn/blog/thermal-imaging/how-infrared-cameras-work, viewed on Mar. 28, 2022.

Harris et al., "Array programming with NumPy". Nature 585, 357-362. https://doi.org/10.1038/s41586-020-2649-2; Sep. 16, 2020; 6 pages.

International Preliminary Report on Patentability for PCT App. PCT/US2021/056482 dated May 2, 2023 (9 pages).

International Search Report and Written Opinion for PCT/US2021/056482 dated Jan. 24, 2022 (16 pages).

Martin Manullang et al. Implementation of Thermal Camera for Non-Contact Physiological Measurement: a Systematic Review. Sensors (Basel). Nov. 23, 2021;21(23):7777. doi: 10.3390/s21237777. PMID: 34883780; PMCID: PMC8659982. Viewed on Feb. 2, 2023.

Nandakumar et al., "Contactless Sleep Apnea Detection on Smartphones," MobiSys '15: Proceedings of the 13th Annual International Conference on Mobile Systems, Applications, and Services; pp. 45-57; https://doi.org/10.1145/2742647.2742674; May 2015; 13 pages.

Non-Final Office Action on U.S. Appl. No. 17/510,357 dated Apr. 11, 2022 (26 pages).

Non-Final Office Action on U.S. Appl. No. 17/510,357 dated Feb. 17, 2023 (42 pages).

Opgal staff writers, Introduction to Infrared (Part 1): The Physics Behind Thermal Imaging, https://www.opgal.com/blog/thermal-cameras/the-physics-behind-thermal-imaging, Apr. 8, 2018, viewed on Mar. 28, 2022.

Prasara Jakkaew et al. Non-Contact Respiration Monitoring and Body Movements Detection for Sleep Using Thermal Imaging. Sensors (Basel). Nov. 5, 2020;20(21):6307. doi: 10.3390/s20216307. PMID: 33167556; PMCID: PMC7663997. viewed on Aug. 1, 2022.

Restriction Requirement for U.S. Appl. No. 17/510,357 dated Jan. 26, 2022 (6 pages).

Reuben Saltzman; "Seek Thermal CompactPRO infrared camera: a home inspector's review;" Startribune.com; https://www.startribune.com/seek-thermal-reveal-pro-camera-a-home-inspector-s-review/; Mar. 7, 2017; 6 pages.

S. Laguela, H. Gonzalez-Jorge, J. Armesto, P. Arias; "Calibration and verifcation of thermographic cameras for geometric measurements;" Infrared Physics & Technology 54, 92-99; Jan. 27, 2011; 8 pages.

Selvaraj et al., "Challenges and opportunities in IoT healthcare systems: a systematic review." SN Appl. Sci. 2, 139, https://doi.org/10.1007/s42452-019-1925-y, Dec. 30, 2019; 25 pages.

So, Adrienne, "Review: Oura Ring," https://www.wired.com/review/oura-ring/, WIRED, Sep. 6, 2020, 7 pages.

Team FLIR, "Resolving Border Security Threats with Integrated Solutions;" https://www.wevolver.com/article/resolving-border-security-threats-with-integrated-solutions; Apr. 4, 2021; 5 pages.

(56) References Cited

OTHER PUBLICATIONS

Team FLIR; "Teledyne FLIR Releases Free Expanded Starter Thermal Dataset for ADAS and Autonomous Vehicle Testing;" Teledyne FLIR, Jan. 19, 2022; 2 pages.

\* cited by examiner

Run

| RUN_ID | uniqueidentifier | PK |
|---|---|---|
| timestamp | datetime | PK |
| patient_ID | int | PK |

Run_statistics

| RUN_ID | uniqueidentifier | PK |
|---|---|---|
| bin_array | float | PK |
| breath_chest | float | PK |
| breath_mouth_nose | float | PK |
| pulse | float | PK |
| temperature | float | PK |
| breath_audio | float | PK |

Events

| RUN_ID | uniqueidentifier | PK |
|---|---|---|
| timestamp | datetime | PK |
| event_type | varchar(50) | PK |

Patients

| patient_ID | In | PK |
|---|---|---|
| patient_name | char(10 | PK |
| patient_age | int | PK |

FIG. 8

CARDIOPULMONARY HEALTH MONITORING USING THERMAL CAMERA AND AUDIO SENSOR

CROSS-REFERENCE TO RELATED APPLICATION

This is a continuation of U.S. application Ser. No. 17/510,357, filed Oct. 25, 2021, which claims priority to U.S. Provisional Patent Application No. 63/107,036, filed on Oct. 29, 2020, each of which is incorporated herein by reference in its entirety for all purposes.

TECHNICAL FIELD

This application relates generally to non-contact health monitoring, and more particularly to non-contact cardiopulmonary monitoring in home and healthcare settings.

BACKGROUND

Acquisition and analysis of cardiopulmonary data is important for judging the health of an individual, such as a sleeping patient. Traditional techniques for monitoring heart rates and breath rates of patients and at-risk subjects require physical contact with monitoring devices. This can make these methods uncomfortable for the patient, and such techniques can otherwise disturb sleep for a sleeping patient. Additionally, health monitoring devices that require physical contact are susceptible to being knocked off inadvertently by a sleeping patient. Further, physical stress and discomfort associated with contact health monitoring devices can introduce error in the final result.

Apparatuses for monitoring subjects during sleep, such as those for conducting polysomnography tests, may be used to diagnose sleep disorder. Such apparatuses are generally bulky, complex and expensive. Sleep tracker devices can be more cost effective, but sleep tracker devices typically require contact with the user and are generally less precise than polysomnography tests.

SUMMARY

What is needed is systems and methods for acquiring and analyzing cardiopulmonary characteristics of a subject that do not require physical contact between the subject and a monitoring device. What is needed is methods for health monitoring of subjects that do not cause discomfort and do not disturb subjects during sleep. Disclosed embodiments provide a cost-effective device for monitoring health, e.g., device suitable for use in the home. The health monitoring device disclosed herein can achieve improved precision in determining cardiopulmonary characteristics of a subject.

Disclosed embodiments employ a health monitoring device to monitor vital signs of a subject, such as a sleeping patient. The health monitoring device may include a thermal camera such as an uncooled microbolometer array to monitor breathing, pulse, temperature, and other vital signs of the patient. An audio sensor, e.g., microphone, may be used for monitoring patient respiratory sounds and other patient sounds. Further information such as blood pressure and heart health can be calculated from these signals and their waveforms. The health monitoring device utilizes the acquired signals and higher order data in analyzing patient conditions and behaviors. Higher order data may include visual data based upon signals output by the thermal camera and audio data based upon signals output by the audio sensor.

In disclosed embodiments, the thermal camera and signal processing of camera outputs track the pulse rate, breathing, and temperature of the subject. In monitoring pulse rate, a thermal camera may sense the sinusoidal motion of the heart rate by imaging the carotid artery in the neck, and the temple. The thermal camera also may sense the sinusoidal motion of the heart rate by imaging the subject's arms and hands. In monitoring breathing, the thermal camera may image one or more of the subject's chest, nostrils, and mouth. In an embodiment, the health monitoring device incorporates an uncooled microbolometer array in communication with a mobile computing device.

In disclosed embodiments, the health monitoring device incorporates audio data in monitoring and characterizing vital signs of a subject. The audio data may include spectrograms in the audio spectrum, such as spectrograms derived from audio clips recorded by the audio sensor. The audio sensor may generate audio signals via microphone, handset, or other transducer that converts sound into an analog electrical signal. The microphone or an external device converts the analog signal into digital audio signals, also herein called audio data. In various embodiments, audio monitoring may be used for monitoring and characterizing breath rate and abnormal respiratory sounds, and for recognizing the subject's speech. In a multimodal method for monitoring the subject, the health monitoring device may activate audio monitoring in the event video monitoring fails to detect presence of the subject at a primary location.

In disclosed embodiments, the health monitoring device includes a processor configured to output a health determination relating to the one or more health parameters of the patient by inputting one or both visual and audio data into one or more machine learning models. In an embodiment, the health determination includes a value of the one or more health parameters, a binary classification of the one or more health parameters, a multiclass classification of the one or more health parameters, an event relating to the one or more health parameters, or a health anomaly relating to the one or more health parameters. In an embodiment, the one or more machine learning models include a supervised learning model including a factorization machine. In an embodiment, the machine learning models include an unsupervised learning model trained to identify key features of interest.

In an embodiment, a monitoring device comprises a set of sensors configured to receive signals pertaining to one or more health parameters of a patient through non-physical contact with the patient, wherein the set of sensors comprise a thermal camera and an audio sensor, wherein the monitoring device is configured to monitor the one or more health parameters of the patient; a signal processing unit configured to generate visual data based upon signals output by the thermal camera and to generate audio data based upon signals output by the audio sensor; and a processor configured to output a health determination relating to the one or more health parameters of the patient by inputting one or both of the visual data and the audio data into one or more machine learning models.

In an embodiment, a method comprises receiving, by a set of sensors, signals pertaining to one or more health parameters of a patient through non-physical contact with the patient, wherein the sensing unit comprises a thermal camera and an audio sensor; generating, by a processor coupled to the set of sensors, visual data based upon signals output by the thermal camera and audio data based upon signals output by the audio sensor; and outputting, by the processor, a health determination relating to the one or more health parameters of the patient by inputting one or both of the visual data and the audio data into one or more machine learning models.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 5 is a schematic diagram of an SQL architecture of features identified via recognition/identification of facial features, according to an embodiment.

FIG. 8 illustrates field names, field data types, and PK primary key values of an example SQL architecture, according to an embodiment.

DETAILED DESCRIPTION

Figure 1:
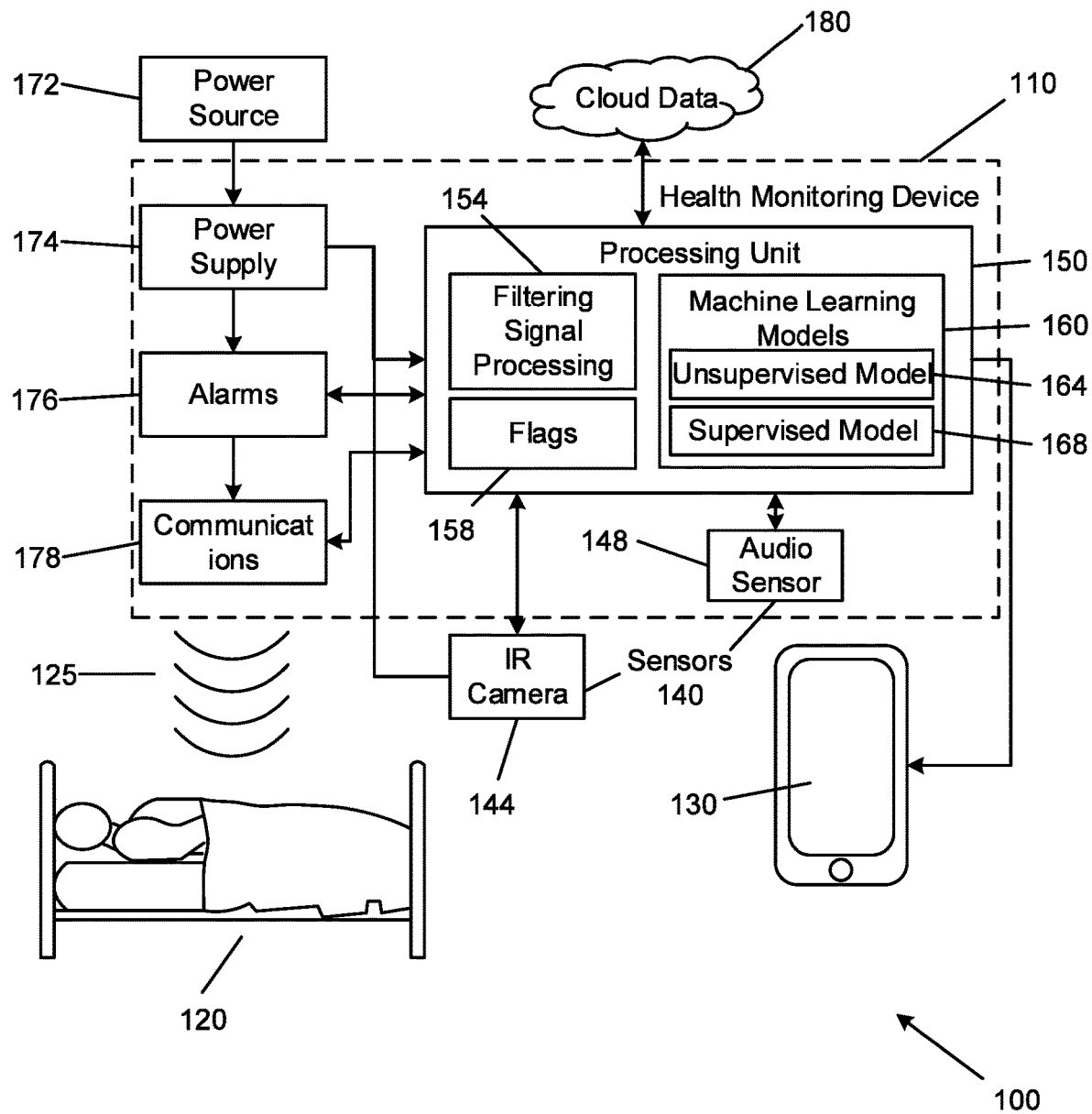
FIG. 1 illustrates an architecture of a non-contact health monitoring device, according to an embodiment.

References will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Disclosed embodiments employ a health monitoring device to monitor vital signs of a subject, such as a sleeping patient. Health monitoring signals may be acquired and analyzed via multiple subsystems to ensure greater reliability. The health monitoring device may include a thermal camera such as an uncooled microbolometer array to monitor breathing, pulse, temperature, and other vital signs of the patient. Further information such as blood pressure and heart health can be inferred from these signals and their waveforms. An audio sensor, e.g., microphone, may be used for monitoring breath rate. An audio recognition system can be trained to characterize abnormal respiratory sounds. The health monitoring device utilizes acquired signals and higher order data as source data for analyzing patient conditions and behaviors. The higher order data may include visual data based upon signals output by the thermal camera, and audio data based upon signals output by the audio sensor.

In disclosed embodiments, the thermal camera and signal processing of camera outputs track the heart rate, breathing, and temperature of a sleeping individual. For pulse rate, a thermal camera may sense the sinusoidal motion of the heart rate by imaging one or both the carotid artery in the neck and the temple. The thermal camera also may sense the sinusoidal motion of the heart rate by imaging one or both the subject's arms and hands. In monitoring breathing, thermal imaging targets may include one or more of the subject's chest, nostrils, and mouth. Together, these signals can be employed in deriving data extrapolating further information about the health of a monitored subject. In an embodiment, the health monitoring device incorporates an uncooled microbolometer array in communication with a mobile computing device.

In disclosed embodiments, the health monitoring device incorporates audio data in monitoring and characterizing vital signs of a subject. Audio data may include spectrograms in the audio spectrum, e.g., spectrograms derived from audio clips recorded by the audio sensor. The audio sensor may generate audio signals via microphone, handset, or other transducer that converts sound into an electrical signal. In an embodiment, the microphone generates AC signals representing air pressure variations of a sound wave, e.g., sounds resulting from speech, breathing, respiratory sounds, or other sounds. The microphone or an external device converts the AC signal into digital audio signals, also herein called audio data. In various embodiments, audio monitoring may be used for monitoring breath rate, for identifying abnormal respiratory sounds, and for recognizing subject's speech. In a multimodal method for monitoring the subject, the health monitoring device may activate an audio mode in the event video monitoring fails to detect presence of the subject at a primary location.

In disclosed embodiments, the health monitoring device includes a processor configured to output a health determination relating to the one or more health parameters of the patient by inputting one or both of visual data and audio data into one or more machine learning models. In an embodiment, the health determination includes a value of the one or more health parameters, a binary classification of the one or more health parameters, a multiclass classification of the one or more health parameters, an event relating to the one or more health parameters, or a health anomaly relating to the one or more health parameters.

An example of a value of one or more health parameters includes systolic and diastolic blood pressure values. An example of a binary classification of one or more health parameters is a binary flag. An example of a multiclass classification of one or more health parameters is a multiclass classification of respiratory sounds. An example of an event relating to one or more health parameters is an apnea event. An example of a health anomaly relating to one or more health parameters is a sleep disorder.

In an embodiment, one or more machine learning models include a supervised learning model trained to recognize features of interest. In an embodiment, a supervised learning model such as regression model includes a factorization machine. In an embodiment, machine learning models include an unsupervised learning model. In an embodiment, machine learning models may refer to methods such as logistic regression, decision trees, Random Forest ensembles, neural networks, linear models, matrix reduction, and/or Bayesian models.

In an embodiment, multiple machine learning models are employed in monitoring health parameters. In an embodiment, multiple machine learning models are combined in multimodal artificial intelligence (AI), in which two or more data types (e.g., thermal imaging spatial data, thermal imaging temperature data, audio data) are combined via multiple AI algorithms. In various embodiments, multiple machine learning models may operate simultaneously or may operate sequentially in monitoring health parameters. In an example of sequential monitoring, a thermal imaging sensor monitors presence of a subject at a primary location. In the event thermal imaging generates a "no patient present" flag, this activates one or more other monitoring modality such as audio monitoring.

FIG. 1 illustrates an architecture of a health monitoring device 100. The health monitoring device includes a set of sensors 140 configured to receive signals pertaining to one or more health parameters without physical contact of the sensors 140 with the subject 120. The sensors 140 are configured to receive signals through non-physical contact 125 with the subject 120. The sensors 140 include a thermal camera 144 that measures the thermal heat of the subject 120 and other objects in the field of view. The thermal camera includes an infrared (IR) sensor, such as a microbolometer array. The set of sensors 140 also include an audio sensor 148.

In the embodiment of FIG. 1, the system 100 monitors health of a sleeping subject 120. The system 100 and its components can easily be adapted to other health monitoring applications that incorporate thermal imaging and audio sensing for monitoring a subject. Other applications may include, e.g., monitoring pilots; car, bus, truck and train drivers; cyclists; automated preliminary health assessment, e.g., for triage in hospital or in doctor's office; infant care; and other individuals, e.g., persons under care of a healthcare worker or care giver. In an example, one or both thermal imaging systems and audio systems track eye motion, heart rate, HRV, breathing rate, and breathing rate variability of a pilot or a professional driver to ensure they are alert and healthy throughout their shifts. In another example, preliminary health assessment/triage metrology for use in hospital and doctor's office settings could be non-contact, self-administered by subject, and could take a few minutes to administer. Mid-infrared imaging (MIR) offers the advantage in various applications that it is not affected by environmental illumination. For example, MIR thermal imaging to observe a professional driver would not be affected by oncoming headlights at night or by occasional glare during the day. Using MIR thermal imaging in a kiosk for preliminary health assessment would not be affected by changing ambient light conditions in a doctor's office.

In various embodiments, thermal camera 144 incorporates uncooled IR image sensors called microbolometers, built around arrays of tiny thermal detectors. In the present disclosure, thermal camera is also referred to as infrared (IR) camera and as microbolometer. A microbolometer is a specific type of bolometer used as a detector in a thermal camera. Infrared radiation in the mid-IR range, e.g., with wavelengths between 7.5-14 strikes the detector material, heats it, and changes its electrical resistance. Arrays of many thermally isolated microbolometers can record images in the thermal IR. This resistance change is measured and processed into temperatures that can be used to create an image. Unlike other types of infrared detection equipment, microbolometers do not require cooling, thereby reducing their cost, size, and complexity. Microbolometers are commercially available in handheld devices, including smartphone cameras.

The use of thermal imaging allows measurement to be performed in a completely dark room so the subject 120 is not disturbed by an external source light required by an optical camera. IR cameras have the advantages that they measure photons radiated from a regarded object, they do not need any external light that may distract or disturb a subject, and they are insensitive to viewing angle.

Health monitoring device 100 may utilize uncooled microbolometer arrays for non-contact measurement of a subject's stance, rate of breathing, temperature, pulse rate and pulse profile. As IR cameras measure radiated photons from a regarded object, they do not need any external light source that can be distracting to the subject 120. Additionally, IR cameras are insensitive to viewing angle. In various use cases, thermal imaging subjects could be pilots; car, bus, truck and train drivers; cyclists; hospital and doctor triage users; and individuals. For drivers, stance monitoring could establish drowsiness, fatigue, inattention or stress.

In an embodiment, signal processing 154 of output of thermal camera 144 may employ functions from OpenCV (Open Source Computer Vision Library) a library of programming functions employed in at real-time computer vision. Using OpenCV, functionalities of facial feature recognition and object recognition are expanded to work with a thermal camera. Features of the face (ducts, eyes, temples, carotid artery, etc.) may each be individually identified using a single shot multi-box detector. In an embodiment, an existing feature map is compared with one or more acquired thermal images. This comparison may include a series of convolutions for feature extraction, with bounding boxes for each relevant feature. By varying the overlap and aspect ratio of sampled features, signal processing may improve performance speed and accuracy.

In an embodiment, signal processing 154 extracts patterns of thermal intensity of sensed features as digital data streams for conversion to frequency domain. This conversion may employ the Fast Fourier Transform used by NumPy. NumPy is a library for the Python programming language including a large collection of high-level mathematical functions to operate on multi-dimensional arrays and matrices. The NumPy library includes the Fourier transfer function Discrete Fourier Transform (numpy.fft). In discrete Fourier transform (DFT), both the original signal and its Fourier transform are replaced with discretized counterparts. The DFT separates its input into components that contribute at discrete frequencies. NumPy Fast Fourier Transform is represented by the following formula:

$$X_k = \sum_{n=0}^{N-1} x_n e^{-i2\pi kn/N}$$

The signal in the Fourier domain typically has a dominant feature that will correspond to the breathing rate or pulse rate. Signal processing 154 may filter the acquired signal via band pass filter around this frequency to improve the signal. In an embodiment, calculated rates are further refined using a factorization machine in machine learning models 160.

The factorization machine fits the calculated rates to appropriate variables, given by the following formula:

$$y(x) = w + o + \sum_{i=1}^{n} w_i x_i + \sum_{i=1}^{n} \sum_{j=i+1}^{n} \langle v_i, v_j \rangle x_i x_j$$

The signal also may be converted to the frequency domain using a wavelet transform. This allows for the signals of interest to change in the frequency domain as a function of time, unlike the more common Fourier transform. Typically, Fast Fourier Transform using a rolling window average is sufficient, however. This is because health monitoring signals most often change slowly with occasional periods of extreme change correlated with a health event.

Because of the large number of physical characteristics that may be derived from information from thermal cameras, a robust supervised learning model 168 is desirable. In an embodiment, model development seeks to find a fitted model and to gain insights into how an arbitrary health feature relates to pulse, breathing, and other physical characteristics. In an embodiment, factorization machine is used as a measurement device that can return an accurate value for training purposes. Data exploration of the calculated factors may identify a relationship between the raw data returned by the camera and the desired value. In an embodiment, processing unit 150 analyzes each frame of dynamic thermal images captured by thermal camera 144.

Figure 2:
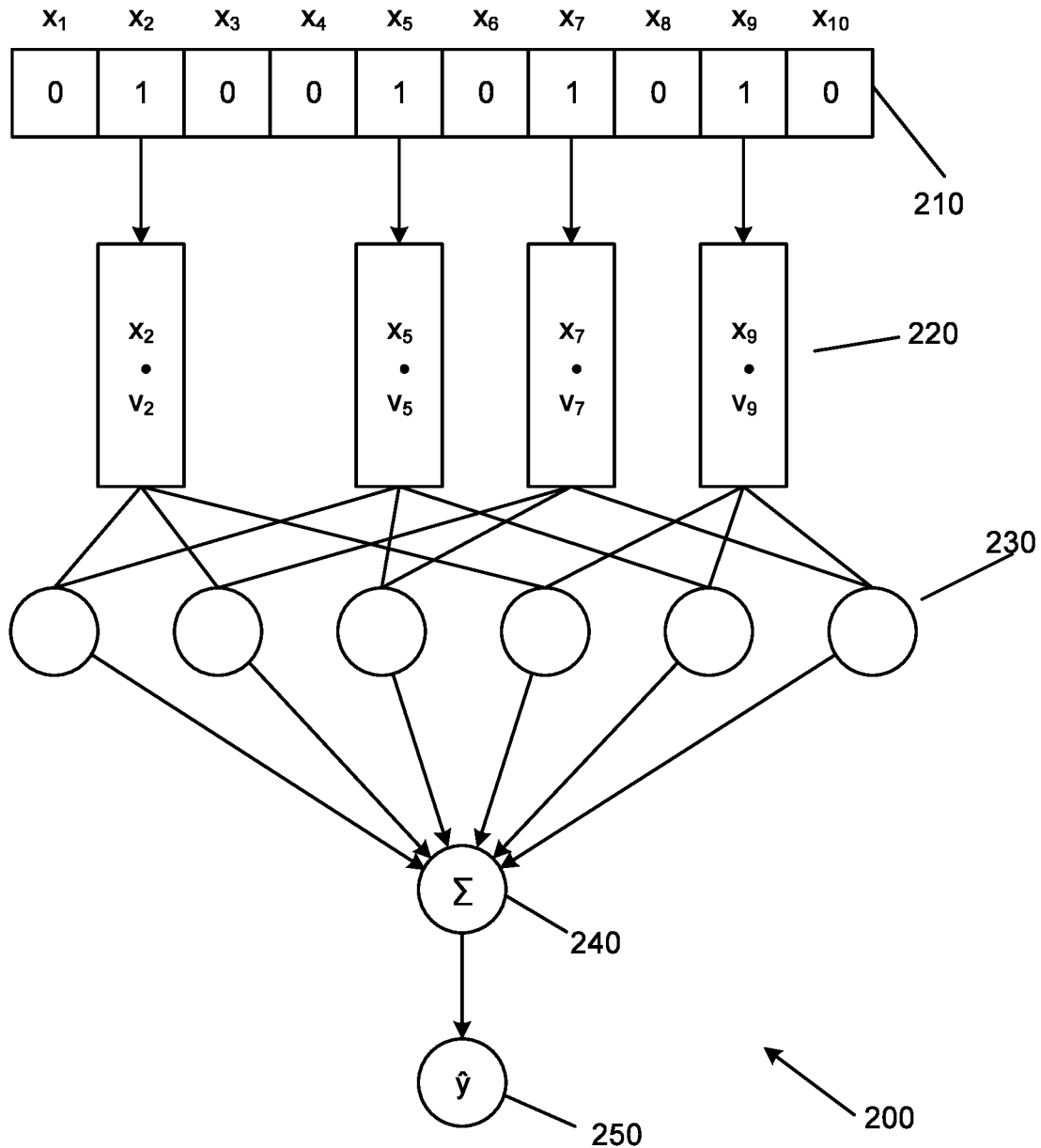
FIG. 2 shows a schematic diagram of a factoring machine, according to an embodiment.

In an embodiment, machine learning models 160 incorporate a factorization machine, as shown in the scheme 200 of FIG. 2. Factorization machines are supervised learning models that can perform both regression and classification. They are non-linear models that model interactions of variables 210 ($x_1$, $x_2$, $x_3$ . . . ) by generating feature vector representations 220 (including vectors $v_1$, $v_2$, $v_3$ . . . ) and by mapping 230, 240 feature interactions to a model output 250 in a low dimensional space. A factorization machine has several advantages over traditional regression techniques commonly employed in machine learning. First, by decomposing a variable into multiple factors, higher order effects, e.g., biological effects, may be observed. Additionally, while a single variable may be over-fitted and thus fail to respond appropriately to a change in the system, a factorization machine is less susceptible to this.

Figure 3:
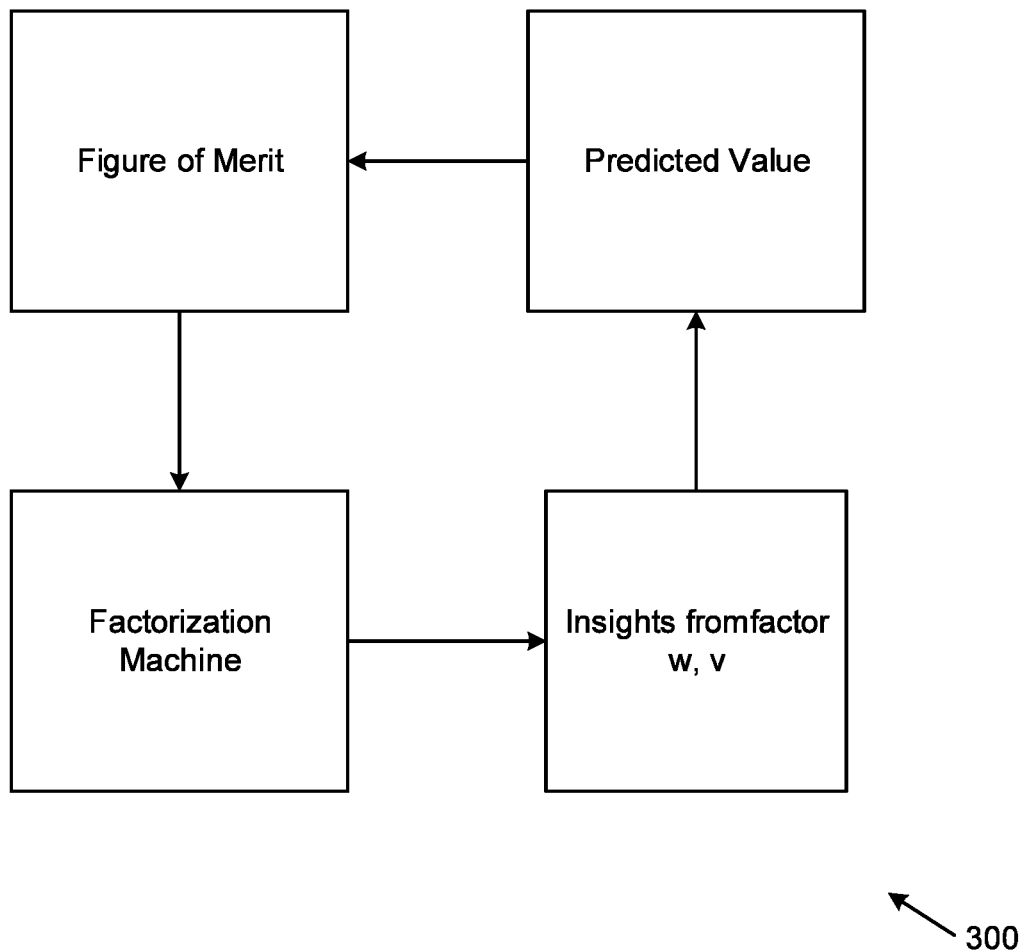
FIG. 3 is a flow chart diagram of recursive processes of a factorization machine, according to an embodiment.

FIG. 3 shows a flow chart of recursive processes 300 of a factorization machine. The factorization machine algorithm employs reinforcement learning that will continually adjust to be in agreement with whatever secondary data stream is being used. A variable "figure of merit" is defined as $|f_p - f|$, where $f_p$ is the predicted value based on the factorization machine. As the factorization machine optimizes this figure of merit, the predicted value will more closely match the ground truth value. Factorization machines can provide supervised machine learning models with excellent interpretability of modeled health parameters. For example, a matrix reduction and averaging procedure can derive matrix-reduced data to reconstruct waveforms with intuitive relevance to health parameters.

In an example of monitoring subject physical characteristics of subject 120, machine learning models apply a factorization machine to determine the subject's tidal volume. As used herein, tidal volume refers to the amount of air that moves in or out of the subject's lungs with each respiratory cycle. Coupled with pulse and breath rate, knowledge of the tidal volume would be an important indication of the subject's health. Under ideal conditions, a sensor may detect a mass of hot, moist air being exhaled, but this technique is sensitive to humidity, ambient temperature, and viewing angle. Instead, by using the motion of the chest, mouth and nostrils, and frequencies as factors, machine learning models may be trained to predict the tidal volume of the breathing. By examining spatial displacement as well as temperature gradients, machine learning models may incorporate contributions of these factors to the overall factorization machine.

To identify motion of the chest, the canny edge detection algorithm with an applied Gaussian filter may be used to determine the motion of the chest, distinguishing the relatively hot body against the cool background. Temperature differences make it straightforward for the algorithm to distinguish between the different temperatures present on the body, which includes covered portions, hands, and hair, relative to the much cooler sheets and blankets. The magnitude and profile of chest motion can be used in training a machine learning model 160, provided with actual measured breath volume, to predict tidal volume. Thus chest motion can be predictive of tidal volume, while the frequency is used to determine breathing rate. This motion can be detected from a variety of angles and under covers.

Figure 4:
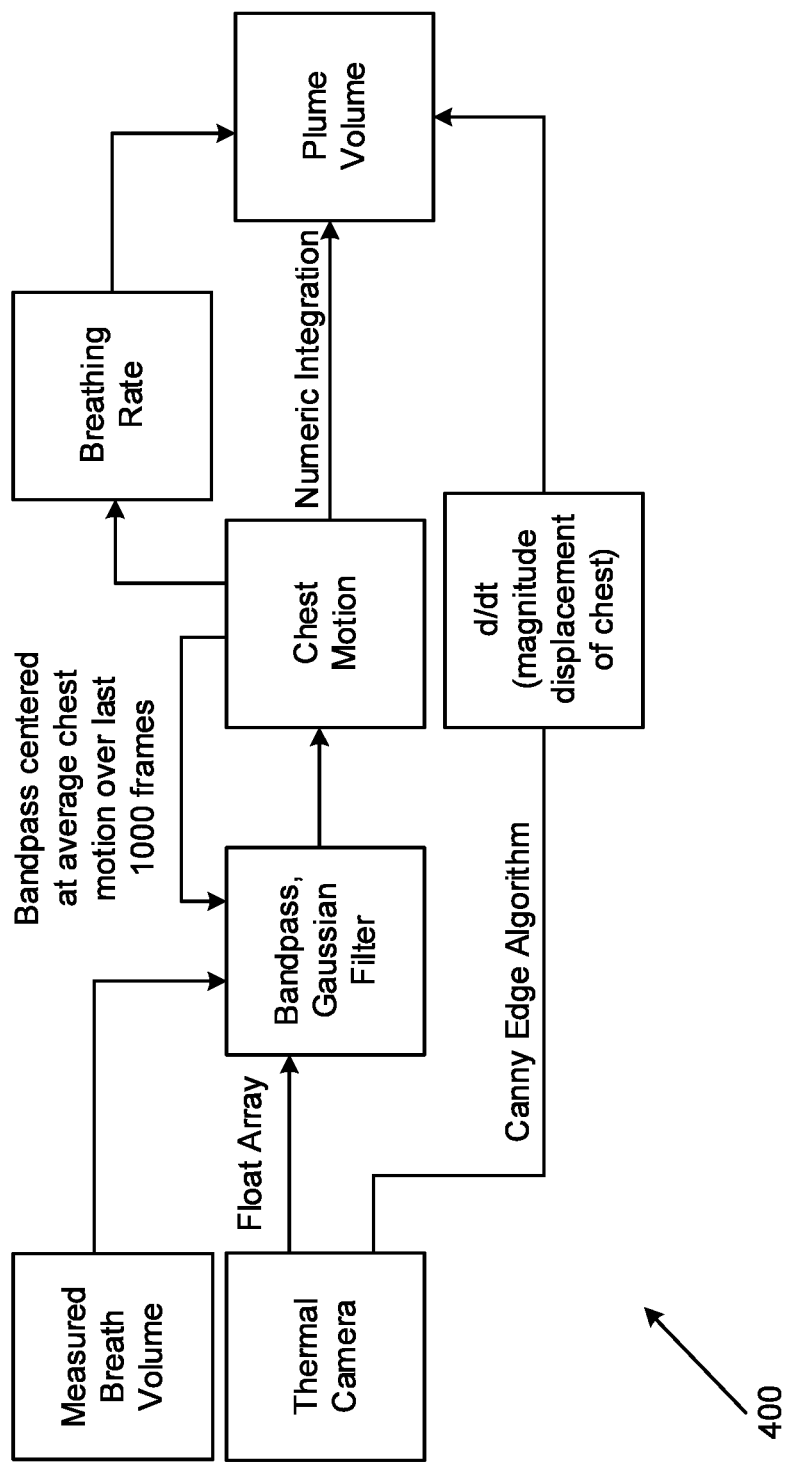
FIG. 4 shows a schematic block diagram of a method for training a chest motion model, according to an embodiment.

FIG. 4 is a schematic block diagram of a method 400 for training a chest motion model. This method takes as inputs measurements of breath volume, and thermal camera output data. Thermal camera output data may comprise a float array. Thermal camera data and breath volume data are passed through a band pass Gaussian filter to derive chest motion. In an embodiment, the band pass is centered at a calculated value for average chest motion over a preceding set of thermal images, e.g., the last 1000 frames. The chest motion data is analyzed to derive breathing rate. The canny edge algorithm may be applied to thermal camera data to derive magnitude of displacement of the chest d/dt. Breathing rate, d/dt, and numeric integration of chest motion are inputs to a model to determine plume volume.

In an embodiment, a computer vision (CV) algorithm may extract the pixels related to each important feature from a digitized thermal image in performing feature recognition of a subject's face and neck. In an embodiment, this algorithm seeks to identify the subject's neck and temples. For each point, all pixels within a certain square radius are used. A weighting function is applied so that the maximum thermal point has the greatest weighting, since presumably this corresponds to the point closest to the artery. Each of these points may be represented by a 2D array that varies in time. FIG. 5 is a schematic diagram of an SQL architecture 500 of features identified via facial feature recognition. Facial feature/element recognition techniques based on thermal imaging methods of the disclosure can derive spatial and temperature visual data that may be used in modeling health parameters.

In an embodiment, health monitoring device 110 analyzes these data points over time to extract information about the heart rate, heart rate waveform, and variability. For a moment in time, each 2D array corresponding to a feature of interest is added to a single array. For two features (neck, temple) with each feature represented by an M×N array, this step results in a 2×M×N array for a given moment in time.

To address noise and many similar data points, CV analysis may perform principal component analysis to extract the most important information from this array. Principal component analysis (PCA) can be calculated several ways, such as truncated singular value decomposition. This PCA technique does not require calculating a matrix inverse. Principal components can be considered a linear projection along the axis such that higher dimensional data is efficiently represented as the function of a single variable. The first principal component corresponds to the axis along which covariance is maximized, and variance is minimized. In CV analysis of images of the carotid artery in the subject's neck and temples, this first principal component represents a stable pulse rate measurement. The second principal component corresponds to maximized variance. In an embodiment, L2-norms (vector distance) of principal components in the data set indicate stability of the measurements of pulse rate variability. If these values change rapidly, further investigation is required.

In an embodiment, the most important feature—the pulse waveform—becomes readily apparent when matrix reduction is performed on successive arrays. This analysis provides an approximate waveform that can be used to calculate its mean, standard deviation, Gaussian spread, and other parameters. These derived data may be employed to construct a blood pressure model. For this purpose, a supervised learning model may take as input a vector of values corresponding to the waveform. A factorization machine then may train the model to fit an experimentally obtained invasive blood pressure for the waveform. Two factorization machines may be used to fit the systolic and diastolic pressures, e.g., as shown in the representative graph 600 of FIG. 6. In a use case, the factorization machines may be applied to qualify and quantify atrial fibrillation and other cardiac ailments.

Figure 7:
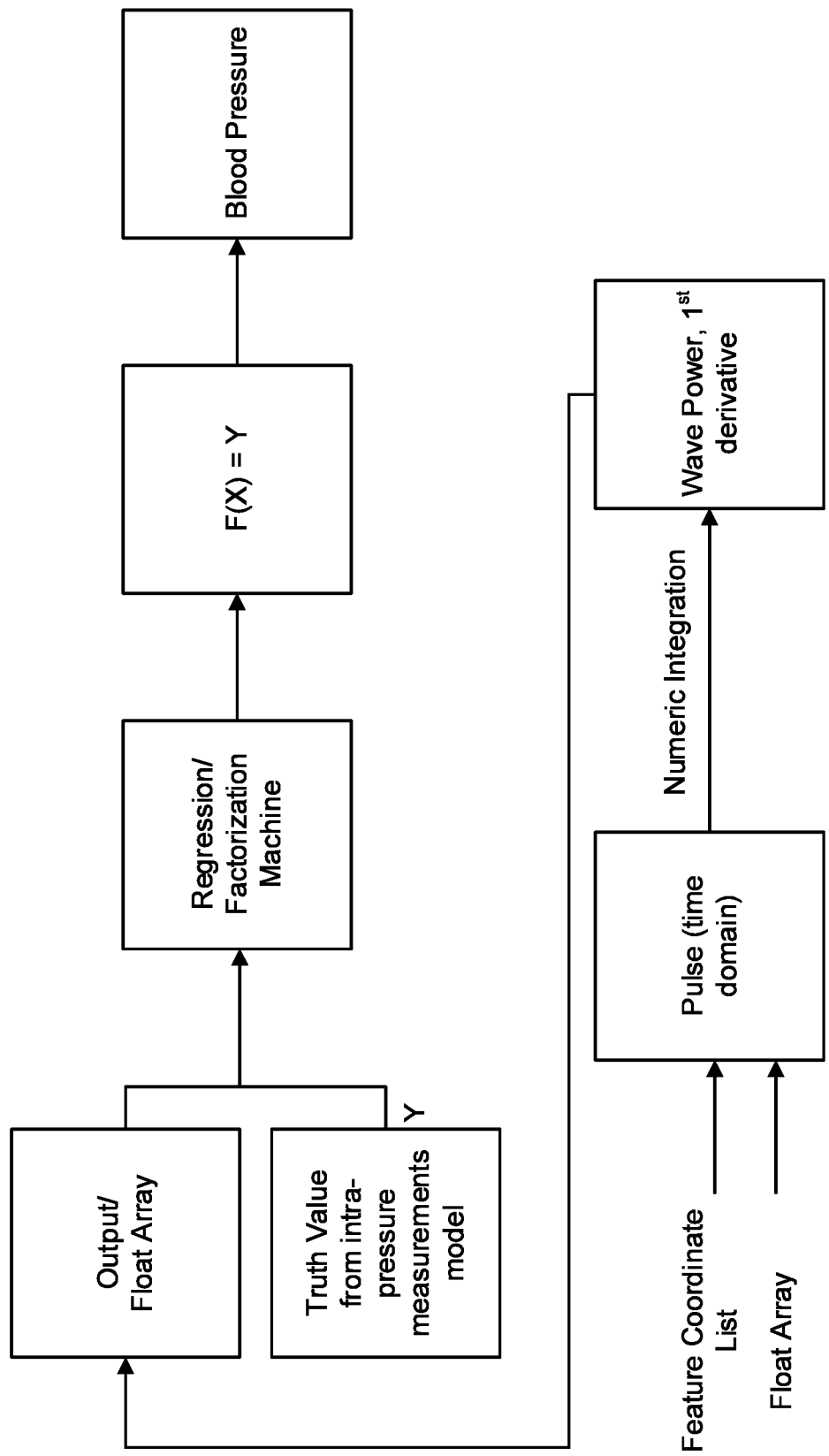
FIG. 7 shows a training process for determining blood pressure, according to an embodiment.

FIG. 7 shows a training process 700 for determining blood pressure. Blood pressure has the systolic and diastolic numbers associated with the waveform of the heart rate. Using the ratio of the rise and fall times, the method 700 can predict these numbers. The method 700 uses blood pressure profile and a secondary source in a supervised learning model to predict blood pressure. The method derives the blood pressure profile by inputting a floating-point array of thermal imaging data and a feature coordinate list to determine pulse data in the time domain. The method applies numeric integration to the time domain pulse data to derive a blood pressure profile, including wave power and first derivative of the pulse data. The blood pressure profile is input to a regression/factorization machine, along with data obtained from a secondary source. In an embodiment, the secondary source includes ground truth data obtained from an intra-arterial measurement method. The regression/factorization machine prediction may be processed (F(x)=Y) to derive modeled blood pressure.

Disclosed embodiments apply CV image processing to respiratory systems, which are lower frequency. Respiratory systems analysis has the advantage that it may incorporate audio data as additional acquired data. For two features, chest and throat movement, with each feature represented by an M×N array, this process derives a 2×M×N array for a given moment in time. In an embodiment, health monitoring device 110 analyzes these data points over time to extract information about breathing rate, respiration volume (waveform), and breathing rate variability.

PCA may be performed to address noise and many similar data points. With the principal component, the most important feature, the breathing waveform, becomes readily apparent when feature movements are represented in successive arrays. The first principal component corresponds to the axis along which covariance is maximized, and variance is minimized. This represents a stable breathing rate measurement. The second principal component corresponds to maximized variance representing breathing rate variability. The L2-norms of the principal components give a sense of stability of the system, e.g., a metric of breathing rate variability such as apnea. If they change rapidly, further investigation is required.

Blood oxygen saturation is another useful medical characteristic that can be determined from thermal imaging. Disclosed embodiments apply similar CV image processing techniques to pulse oximetry of blood oxygen saturation. Thermal imaging outputs an approximate waveform that may be analyzed via CV techniques to calculate its mean, standard deviation, Gaussian spread, and other characteristics.

In an example, these visual data are employed in constructing a blood oxygen saturation model. A supervised machine learning model may take as input a vector of values corresponding to the waveforms. A regression/factorization machine trains the model to fit experimentally obtained via oximeter measurements for the waveform. Oximetry is a traditional technique in which blood oxygen saturation is measured by passing light through a fingertip and comparing the absorption of the light through oxygenated versus unoxygenated blood. Here oximetry is used as ground truth in training the blood oxygen saturation model.

Respiratory system analysis may incorporate audio data, such as spectrograms in the audio spectrum, in addition to the vision data. Although these audio data have different units, supervised learning models may be trained to convert between them. Adding audio spectrum values to the thermal imaging values in a factorization machine may enable the factorization machine to automatically learn relationships between audio variables and thermal/spatial variables. In an example, this procedure was applied to three features with each feature represented by an M×N array and a 3×M×N array for a given moment in time.

In an embodiment, health monitoring device 110 communicates with a mobile computing device, e.g., smart phone 130. The mobile computing device may act as power source and device to compute signals. In an embodiment, raw data is processed on the phone, and derived signals and flags 158 are saved remotely when the run is stopped. A mobile computing device 130 also may perform calculation for real-time monitoring of vital signs. Device 130 includes sufficient RAM and computing power to undertake all real-time simultaneous modeling and statistical analysis. In an example, a code base for smartphone 130 was developed in python, C, and C++, and converted using public cloud computing tools provided by Microsoft Azure. The viewing angle may also be easily chosen with simple wall mounts in a wide variety of settings.

Using smart phone 130 as processor provides a cost-effective design for health monitoring applications, such as monitoring subject 120 during sleep. Other health monitoring applications may replace smart phone 130 with another computing device suitable for the application. In applications in which monitoring subjects could be pilots, car, bus, truck or train drivers, the health monitoring processor may be included in a vehicular computer system. In systems for hospital and doctor triage of patients, the processor may be included in a device such as a kiosk.

The use of a smart phone or other mobile device 130 can extend sensing capabilities for health monitoring of a subject. In an example, a back facing camera of a smart phone effects video imaging in visible light spectrum of neck and temple of a subject to track and create blood pulse profile. These optical sensor readings can provide measurements of pulse rate and pulse rate variability as inputs for predictive modeling of systolic and diastolic blood pressures.

Processing unit 150 can be implemented using a single-processor system including one processor, or a multi-processor system including any number of suitable processors that may be employed to provide for parallel and/or sequential execution of one or more portions of the techniques described herein. Processing unit 150 performs these operations as a result of central processing unit executing software instructions contained within a computer-readable medium, such as within memory. As used herein, a module may represent functionality (or at least a part of the functionality) performed by a processor.

Device 100 includes a power supply 174 for powering components of health monitoring device 110, including the mobile device 130 and IR camera 144. In an embodiment, power supply 174 is a battery that can be recharged by power source 172, e.g., via continuing mains feed charging. Power supply 172 may be configured to provide non-interruptible operation during power outs.

Communications module 178 may support various wired and wireless various communication protocols such as Transmission Control Protocol and Internet Protocol (TCP/IP), User Datagram Protocol (UDP), and IEEE communication protocols, and standard wireless protocols such as Bluetooth®, BLE, Wi-Fi, NFC, ZigBee®, and the like. BLUETOOTH is a registered trademark of Bluetooth Sig, Inc., Kirkland Washington. In one example, communication protocols may include wireless communications according to BLUETOOTH specification sets or another standard or proprietary wireless communication protocol. In another example, communication protocols may also include communications over a cellular network, including, e.g., a GSM (Global System for Mobile Communications), CDMA (Code Division Multiple Access), or EDGE (Enhanced Data for Global Evolution) network. Cellular communications may accommodate operational and system uploads, real-time alarm monitoring outputs to healthcare professionals and care givers, session reports archiving, and reporting to healthcare professionals and care givers. In an example, wireless fidelity (Wi-Fi) communications may accommodate functions such as operational and system uploads, real-time alarm monitoring outputs to healthcare professionals and care givers, session reports archiving, and GP/care giver reporting to healthcare professionals and care givers. In a further example, communication protocols may include wired duplex communications with IR camera 144.

Audio sensor 148 may generate audio signals via microphone, handset, or other transducer that converts sound into an electrical signal. A microphone converts the air pressure variations of a sound wave, e.g., resulting from speech, breathing, or other respiratory sounds from subject 120. Microphones convert sound waves into AC electrical audio signals and are therefore analog devices. In disclosed embodiments, analog signals from audio sensor 148 signals are converted to digital audio signals processed by filtering/signal processing module 154. A microphone or other transducer may output digital audio signals via built-in analog-to-digital converters, or may be coupled to an external analog-to-digital converter device that outputs digital audio signals.

Audio monitoring may be used for monitoring breath rate, and may be trained to identify abnormal respiratory sounds. Audio monitoring can measure various physical attributes: frequency, e.g., the number of the sound waves or vibrations per second; intensity or amplitude, e.g., the height of sound waves from their mean; and quality or timbre. Quality or timbre differentiates two sounds with the same frequency and intensity. The timbre of a sound depends on its wave form, including the number of overtones or harmonics, their frequencies, and their relative intensities (amplitudes).

In an embodiment, audio sensor 148 is used to obtain audio intensities and other audio parameters of breathing, which may provide an additional signal to confirm the accuracy of vision analysis of chest motion and breathing. In an embodiment, filtering/signal processing module 154 passes the audio signal to the frequency domain, in which a large magnitude signal is taken as the breathing rate. Module 154 may filter out background noise, as most sounds are broad-bandwidth, low intensity in nature. If several prominent peaks occur in the frequency spectrum, the peak closest to the frequency of breathing calculated by the chest and throat motion and exhalations is chosen as the target feature in performing band pass filtering.

In order to distinguish between sounds from two sleeping individuals, a digital band pass filter may be employed. This procedure identifies the two frequencies with the greatest magnitudes, corresponding to breathing of the two individuals. The original signal is duplicated then passed through band pass filters centered at each of these two frequencies in order to find the breath rate for each person. The band pass filters may filter out extraneous noises that might briefly conceal breathing sounds, such as thunder or vehicle noise. In an example, the central frequency of the band pass filter is calculated via a rolling average, in which the frequency of a preceding time interval (e.g., previous 5 minutes) is used. This ensures that the signal is not lost if, over the course of a night, the breathing slows, as might be expected.

For the purpose of diagnosing adventitious lung sounds, e.g., sounds associated with respiratory diseases, filtering/signal processing module 154 does not perform band pass filtering since training models use higher-order overtones are used as inputs.

Flags 158 may be classified into several categories. If the patient leaves the frame, the temperature sensed by thermal camera 144 will drop to ambient bed temperature. This flag will note the patient has left the bed. If the maximum temperature in frame remains surface temperature, but the position of sleep impedes one or more signals, the flag will note which signals are impeded and attempt to make a guess as to why, with the position of the sleeping patient and pillows and blankets covering them being two possibilities. These regions are distinguished by their relative temperatures. Further, in the event a signal is lost for no obvious reason, processing unit 150 can check motion data during the preceding time period (e.g., five minutes). Motion may be measured, e.g., by the displacement vector of the canny edge. If this metric falls below a percentage threshold, it may be assumed some system error is responsible. In this case, the temporarily saved data may be stored in a data log for the night.

In an embodiment, audio signal 148 is analyzed to recognize the subject's speech. In an example, speech recognition employs Carnegie Mellon's Hephaestus Speech-related software systems to throw flags 158 when key phrases, such as "help" or "I've fallen," are spoken. Using a recurrent neural network, the spectrograms of these audio clips are passed through a triangular Mel filter, which weights frequencies dominant in human vocalizations. The filtered spectrograms are subsequently trained in a supervised learning model. Key phrase flags 158 may trigger alarms 176, such as audible alarms or visual alarms displayed to healthcare professionals and care givers. In an embodiment, system 100 may acknowledge that 'cries' were received over phone speaker 130. In an embodiment, keyword recognition can be used to begin a monitoring run and/or to end a monitoring run.

In an embodiment, the visual system 144, 154 includes a patient presence model that identifies when no subject 120 is in the field of view, e.g., generating a "no patient present" flag. When this is the case an additional audio monitoring measure 148, 154 is activated, e.g., to identify falling sounds and sounds likely to occur when a patient rises, e.g., doors opening and closing, and toilet flushing. A fall has a broad spectrum, making it an impracticable measure to track continuously. Using the same technique as identifying other audio phenomena, monitoring for fall stops once the patient is in the field of the view of the camera. If a fall occurs, a flag 158 is thrown and care givers are notified 176. Other modalities may be activated by "no patient present" flag, such as activating a front facing camera and directing local WiFi to turn on lights in a room. These additional modalities may be deactivated if the video system later detects patient presence.

In an embodiment, if a signal is not found within a predetermined confidence interval, a flag 158 is thrown to indicate a signal has been lost. If the maximum temperature sensed by thermal camera 144 is below 25° C., it can reasonably be inferred the patient has moved out of the field of view, and the flag thrown notes this. All flags thrown over the course of a night may be saved to a text file as well as to a data log for the time of each flag. In an embodiment, frame data may be saved for a limited time (e.g., 5 minutes) before being replaced, while attributes derived from the frame data may be stored in a data log for the night.

In an embodiment, standard deviation, first and second derivative, and splining fit are all stored by default. These data have various applications in determining patients' health. Using the derivative and standard deviation, health anomalies such as apnea and atrial fibrillation can be discovered and flagged 158, which may result in an alert 176 to a healthcare worker or care giver. In a use case, this system serves as a smart monitor to aid nurses and nightstaff in rest home and hospice settings. In an embodiment, a flag 158 is a binary classifier for which minimizing false negatives are prioritized over minimizing false positives. Model training may select weighting errors to provide a priori Bayesian distributions for probabilistic alerting of healthcare workers. Model training may employ joint probabilities to allow incorporating other signals relevant for the patient's health.

The system 100 may store data in local databases of health monitoring device 110 and mobile computing device 130. The system also may store data, e.g., archived data, in cloud databases 180. Cloud 180 may be a third-party cloud. Databases are organized collections of data, stored in non-transitory machine-readable storage. The databases may execute or may be managed by database management systems (DBMS), which may be computer software applications that interact with users, other applications, and the database itself, to capture (e.g., store data, update data) and analyze data (e.g., query data, execute data analysis algorithms). In some cases, the DBMS may execute or facilitate the definition, creation, querying, updating, and/or administration of databases. The databases may conform to a well-known structural representational model, such as relational databases, object-oriented databases, or network databases. Example database management systems include MySQL, PostgreSQL, SQLite, Microsoft SQL Server, Microsoft Access, Oracle, SAP, dBASE, FoxPro, IBM DB2, LibreOffice Base, and FileMaker Pro. Example database management systems also include NoSQL databases, i.e., non-relational or distributed databases that encompass various categories: key-value stores, document databases, wide-column databases, and graph databases.

Data management is an important consideration for system 100. A floating-point array with approximately 100,000 returned at a frequency of 15 Hz could indicate that it is not practical to store all data. In an embodiment, a SQL-based architecture is used to ensure the important vital signs are saved. Each frame may be pushed into a stack, with the newest frame replacing the oldest, with the length of the stack determining how many full-frames are stored, e.g., 10,000. FIG. 8 illustrates field names, field data types, and PK primary key values of an example SQL architecture.

Another system design consideration is sampling rate, per Nyquist's Theorem. The discrete nature of sampling may be fitted to assumed continuous functions as a splining curve whose higher-order terms could be useful for determining additional data.

One goal of disclosed systems and methods is to extrapolate general diagnoses from data collected. A corpus of data collected over many patients concerning their breathing rate, pulse, lung capacity, and sleep cycle may offer deeper insights into the well-being of monitored patients. In an embodiment, the system applies data mining methods to create correlation matrices. Correlation matrices may be used to describe the health of a patient and to identify higher risk conditions of the patient based on covariance. Upon interpolation to continuous functions, higher-order terms may correspond to physical phenomena such as the correlation of blood pressure with pulse waveform.

The multiple ways in which breathing is recorded, including chest motion and audio, supports application of Bayesian machine learning on the signals. Given a value determined by one method, ideally other methods should have the same value. Machine learning modeling 160 may calculates the posterior distribution of each pair to determine which signal is most likely flawed. This information can then be used to adjust the neural network and filters that determine that signal. Bayesian machine learning then can compare the signals again to find better agreement.

Figure 9:
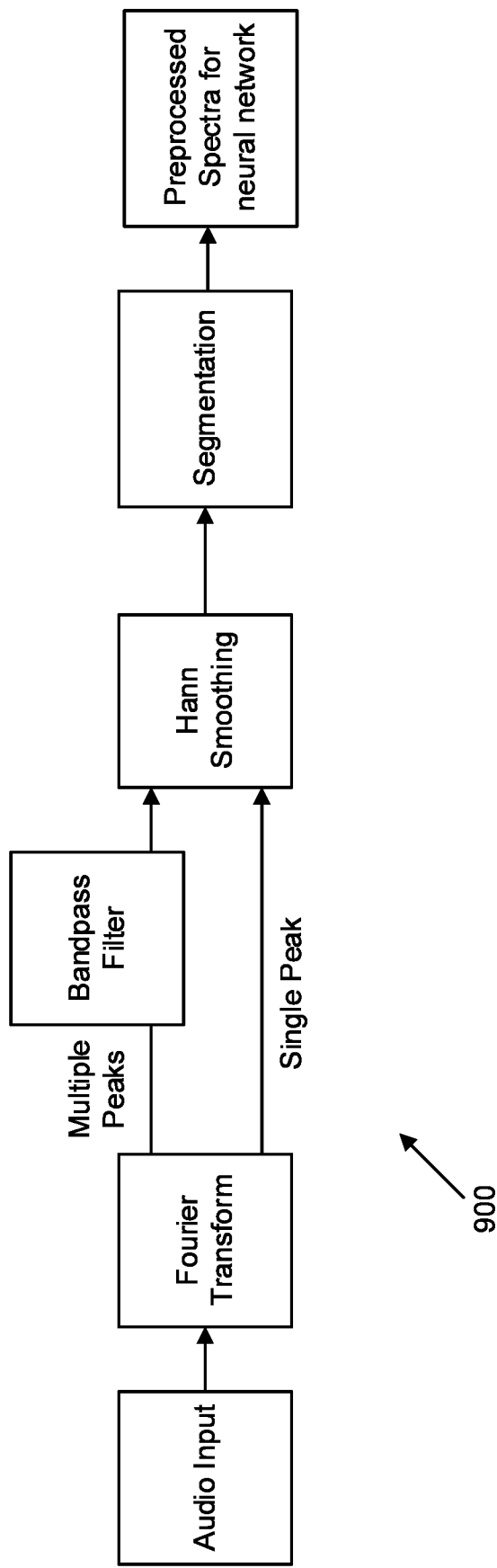
FIG. 9 illustrates an audio pre-processing method for identifying respiratory ailments, according to an embodiment.

Disclosed embodiments may apply audio monitoring to recognize coughs. Coughs are typically characterized by three phases: an initial loud, peak in intensity, followed by a quick attenuation and finally a voiced phase. A recognition algorithm may consider the number of cough sounds, the portion of breaths that include or are disrupted by a cough, and cough epochs, defined herein as the number of coughs with no more than two second interval between them. Chest movement is a further classifying parameter. Also pertinent are the audio breathing phase analysis and chest dynamics for characterizing asthma, pneumonia, and other abnormal respiratory conditions. FIG. 9 illustrates an audio pre-processing method 900 for identifying respiratory ailments.

Small airways' obstructions are the most important clinical features of bronchial asthma, pneumonia, and Chronic Obstructive Pulmonary Disease (COPD). Respiratory sounds, which may be generated by turbulent and laminar air flows in the airways of different diameters, provide invaluable information concerning the pathological processes in pulmonary tissue or airways. Changes of airway characteristics caused by a disease lead to the appearance of specific additional noises in the respiratory sounds, also referred to herein as adventitious lung sounds.

In computer-based respiratory sound analysis, adventitious lung sounds may be classified in frequency bands, e.g., low frequency (100 to 300 Hz), middle frequency (300 to 600 Hz), and high (600 to 1,200 Hz) frequency bands. Frequency is measured objectively, while pitch is the subjective perception of sound's frequency.

Adventitious lung sounds include abnormal respiratory sounds such as wheezing, stridor, pleural, squawk, and chronic cough. Respective sounds are distinct and readily characterized. Tracheal sounds are harsh, loud, have high pitch, and are usually hollow and tubular as they are generated by turbulent airflow passing through the pharynx and glottis. Wheezes are high-pitched sounds due to airway narrowing that causes airflow limitations as with asthma. Rhonchi sounds are low-pitched related to the thickening of mucus in the larger airways as with bronchitis due to the secretions in the bronchial trees. Stridor are high pitched sounds generated by turbulent airflow in the larynx or bronchial tree, and are related to an upper airway obstruction as with epiglottitis, croup, and laryngeal edema. Inspiratory gasp sounds or whoops, e.g., after a bout of coughing, are caused by fast moving air through the respiratory tract and a pathognomonic symptom of whooping cough (pertussis). Squawks, or short wheezes, are generated by oscillation at the peripheral airways and associated hypersensitivity to pneumonia. Fine crackle sounds are caused by explosive openings of the small airway and usually associated with pneumonia, congestive heart failure, and lung fibrosis. Coarse crackle sounds are generated by air bubbles in large bronchi and can be heard on patients with chronic bronchitis, bronchiectasis, as well as COPD. Pleural rub sounds are non-musical rhythmic sounds due to the rubbing of pleural membranes when breathing and are usually caused by inflammation of the pleural membrane. These qualitative differences can be rigorously characterized by their respective spectrums. Chest and throat video dynamics typically correlate, particularly for respiratory events associated with lower frequency sounds.

System 100 includes tools for training machine learning models for the diagnosis of lower respiratory tract disease, upper respiratory tract infection, pneumonia, bronchiolitis, croup, asthma exacerbation/reactive airway disease, chronic obstructive pulmonary disease, chronic obstructive pulmonary disease exacerbation and obstructive sleep apnea. Potential use cases include healthcare providers in telehealth, emergency department, urgent care and primary care settings as well as humanitarian facilities in the developing world.

Figure 10:
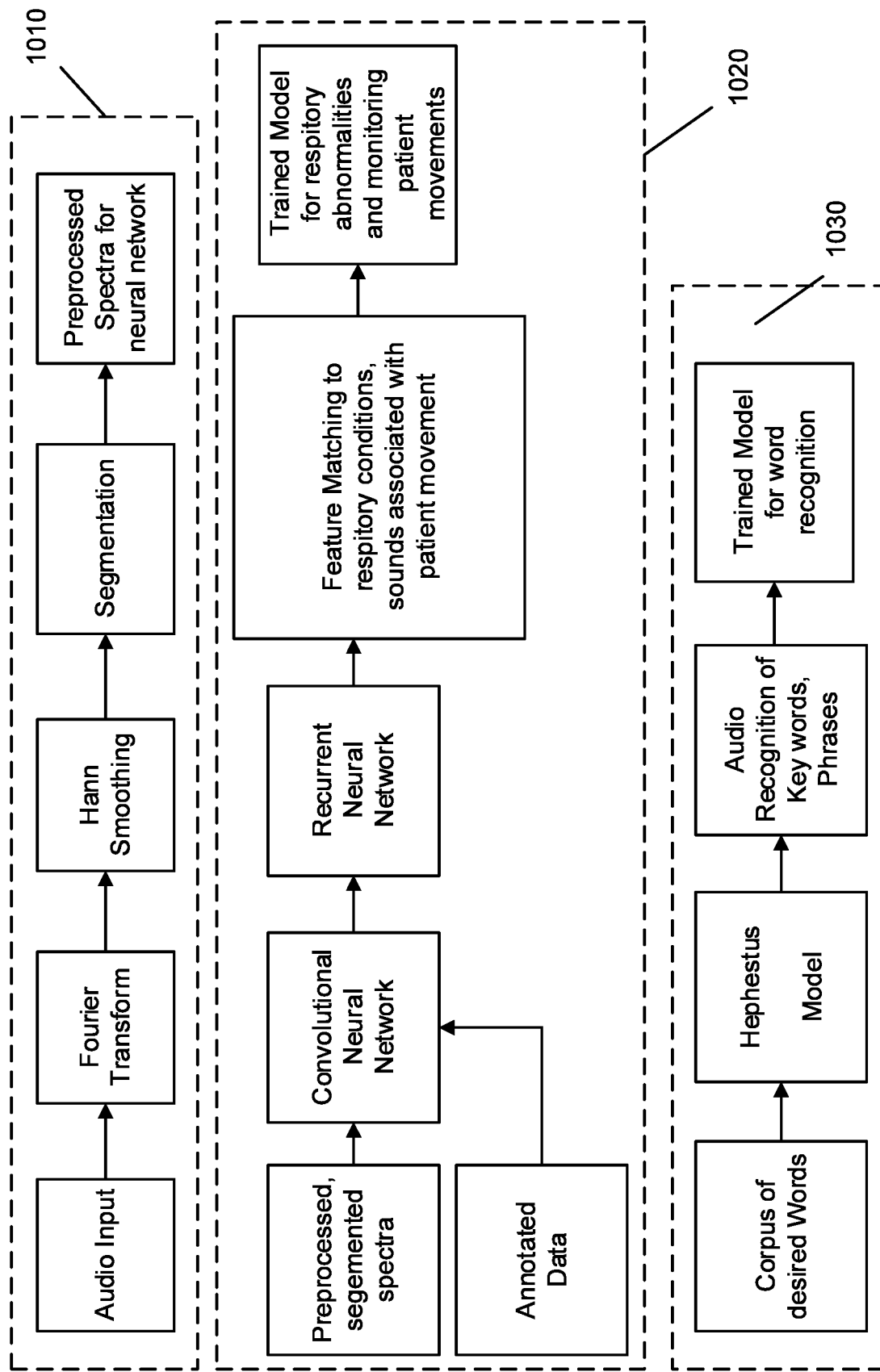
FIG. 10 is a flow chart diagram of training methods for analysis of audio events, according to an embodiment.

FIG. 10 is a flow chart diagram 1000 of training methods for analysis of audio events. Process 1010 applies Fourier transform and Hann smoothing to audio input signals. Process 1010 then performs segmentation to produce pre-processed audio spectra, e.g., for neural network modeling.

Process 1020 trains a model to identify respiratory conditions and patient movements. Process 1020 inputs pre-processed, segmented spectra from process 910 along with annotated data into a convolutional neural network (CNN). The CNN may be trained as a recurrent neural network, a network in which connections between nodes form a directed graph along a temporal sequence. In an embodiment, the CNN performs feature matching to respiratory conditions and to sounds associated with patient movements.

Processes 1010, 1020 illustrate an approach to acquisition and analysis of adventitious lung sounds, which may signify pathological processes in pulmonary tissue or airways. This approach employs a convolutional neural network to classify spectrograms. The respective spectrograms of relevant sounds are preprocessed via Hann smoothing. Hann smoothing generally has the advantage of removing broad spectrum, low intensity noise that may be present from traffic, television, or weather. The recordings are split into samples, e.g., 1 second samples, and are identified using a deep convolutional neural network. Processes 1010, 1020 also encompass harmonics of the fundamental frequency present from breathing. Using a regression classifier model, higher order harmonics correspond to additional parameters fitting the model to the sounds, with the constant term in the model being the natural breathing rate.

Process 1030 trains a model for word/phrase recognition. Processes input a corpus of keywords and key phrases. Process 1030 applies the Hephaestus model for audio recognition of keywords and key phrases.

In addition to audio analysis of respiratory rates, health monitoring methods disclosed herein utilize two additional independent metrics to assess and classify respiratory effort (depth of inspiration) and tidal volume estimations from chest movement modelling. These metrics are N/M expiration and chest and throat movement. Real-time processing algorithms can offer fundamental information in detection and classification of adventitious sounds and can enable timely identification of diseases, as well as changes in their severity.

Physical characteristics that may be derived from raw frame data of thermal sensor 144 include breath-rate waveforms. The area feature (integral under period), distance feature (period), and their derivatives can operate at between 0-6 Hz and have medical applications. In an embodiment, calculating the waveform for both features follows a similar procedure ("shift-sum procedure"). A filter is not suitable because the waveform is a complex, multi-peaked function. Therefore, to reduce noise and ensure the waveform is properly populated, the average period is calculated over a time interval (e.g., 5 minutes). If the standard deviation is too high, the waveform is not calculated because the period is changing which indicates the patient's vital signs are shifting. If the average period remains similar, each period is transformed according to $\sin(w(t-nT))$, where n is the period number and T is the average period. Using this procedure, all waveforms nearly coincide and a waveform with a large sample set and low uncertainty may be obtained.

In the present disclosure, heart rate refers to the number of times a subject's heart beats per minute. Heart rate variability (HRV) measures the time between each heartbeat, also called an R-R interval in ECG signals. Beat-to-beat interval variation may be measured in milliseconds and can vary depending on a number of factors. For instance, the interval between heartbeats is generally longer while exhaling and shorter while inhaling. Various factors can influence or change a subject's HRV metrics, such as exercise volume and intensity, chronic health conditions, quality of sleep, and diet. Another reason for HRV is operation of the autonomic nervous system, which controls the involuntary aspects of physiology, via two branches, parasympathetic (deactivating) and sympathetic (activating). HRV is an extremely sensitive metric that fluctuates greatly throughout the day, from one day to the next, and from one person to another. Younger people tend to have higher HRV than older people, and males often have slightly higher HRV than females. Elite athletes usually have greater HRV.

In view of relationships between HRV and various health conditions, quality of sleep, and diet, this metric is utilized by numerous contact health sensing devices. In contrast, non-contact health monitoring systems and methods of the present disclosure can measure HRV directly from blood pressure pulse profiles representing heart hydraulic performance, which can be more informative than EKG pulse commands.

Sudden hemodynamic instability (HI) due to cardiovascular and/or cardiorespiratory distress is a common occurrence. Causes can include hemorrhage, sepsis, pneumonia, heart failure, and others. Due to the body's compensatory mechanisms, heart and respiratory rate, and blood pressure can be indicators of HI. When detected late or left unrecognized, HI can lead to complications and even death. Signs of hemodynamic instability include having arterial systolic blood pressure<80 or >220 mmHg, a diastolic blood pressure of >110 mmHg, a pulse rate of <40 or >160, a respiratory rate of <8 or >36, a $SpO_2$<90%, and temperature. Pulse rate variability (PRV) has been demonstrated to reflect status of the autonomic nervous system. Pulse rate has been identified as a minor indicator, while PRV has been shown to indicate significant perturbations.

Non-contact monitoring methods disclosed herein may be employed in accurately predicting problems before they occur. This capability can aid in diagnosis and treatment of a deteriorating patient. In various embodiments, these predictions may be based on one or more metrics including core temperature from thermal imaging; respiratory rate from audio; thermal/spatial analysis of mouth, nose and chest analysis; and respiratory volume from spatial chest analysis. These real-time measurements can provide a rich and comprehensive data set for training a machine-learning HI predictor to improve model performance. Additionally, ECG is a contact non-invasive device while embodiments disclosed herein provide a non-contact device. In use cases, a non-contact HI prediction model could be deployed to monitor patients at home, in the field and even while driving.

In another application, disclosed embodiments may be applied to understand disordered sleep of a subject in order to identify a solution. Disordered sleep varies considerably from person to person and can be of a physiological and psychological nature. A disrupted biorhythm, poor sleep posture, lowered resilience to stress, and psychological distress such as worry about being able to fall asleep all can lead to sleep disruption. In an embodiment, disclosed embodiments may apply measurements of breathing rate and breath volume and could implement a feedback function to reduce breathing rate. This process may output an audio signal via mobile device 130 or via Bluetooth ear buds. Remedial measures could include, e.g., reducing pulse rate, and implementing an audio meditation session to induce sleep.

A photoplethysmogram (PPG) is an optically obtained plethysmogram that can be used to detect blood volume changes in a microvascular bed of tissue, effectively a spatial measurement. Systems and methods of the present disclosure provide thermal plethysmogrammy (thermal PG), offering various advantages over optically obtained plethysmogram. Optical PPG is much noisier and indistinct than thermal PG, and only thermal PG can identify the end and start of diastolic pressure pulses. PPGs acquired at finger or wrist have much more damped and indistinct pressure pulse profiles than are available from thermal PG acquired at arteries at temple, neck or upper arms of a subject. In a use case, a machine learning model 160 may input thermal PG data to estimate diastolic pressures.

Figure 6:
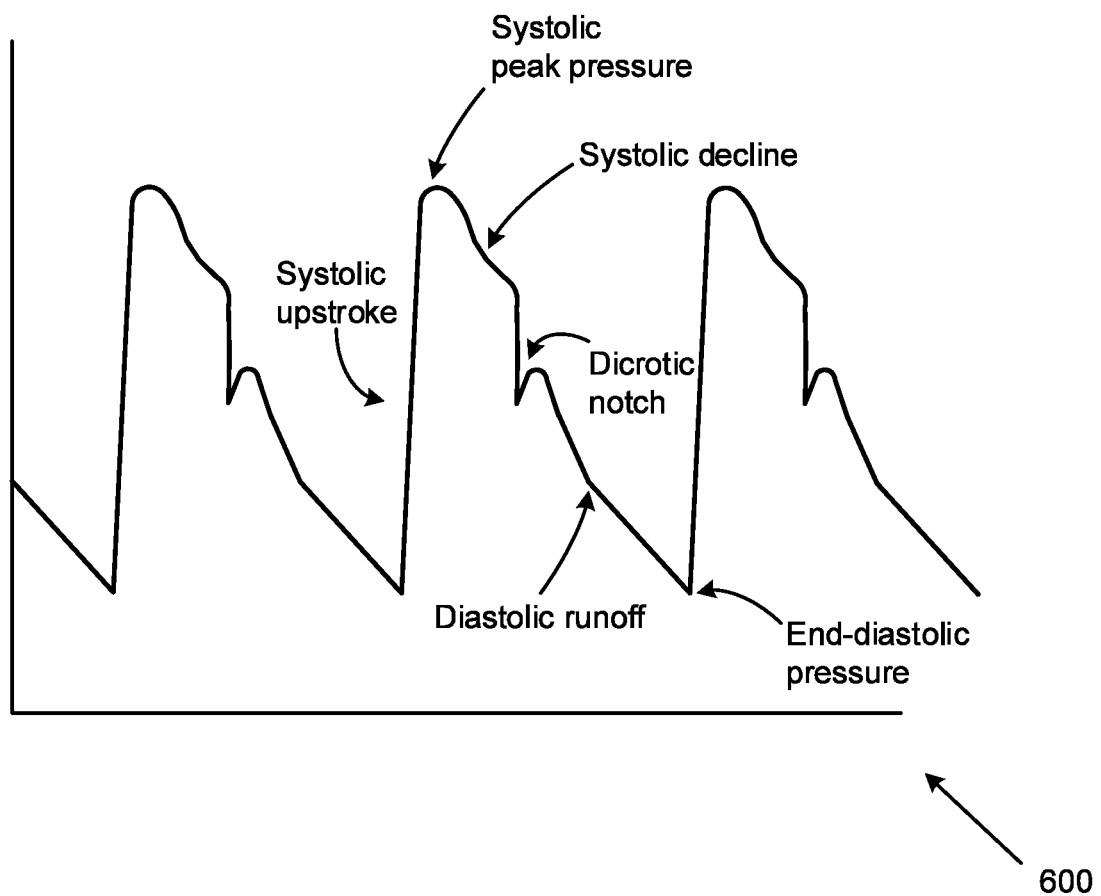
FIG. 6 is a representative graph of a blood pressure waveform including systolic and diastolic pressures, according to an embodiment.

Blood pressure has systolic and diastolic numbers associated with the waveform of the heart rate (FIG. 6). Using a blood pressure profile and a secondary invasive pressure measurement device, a supervised learning model may be used to predict blood pressure from the thermal PG system. Given a reasonable accurate characterization of the waveform, model exploration can investigate its properties to infer the atrial fibrillation of the patient.

Pulse shape and energy of the heart may be derived from the raw frame thermal PG data. The area feature (integral under period), distance feature (period), and their derivatives can operate at between 0-6 Hz and have medical applications. In an embodiment, calculating the waveform for both features follows a similar procedure (herein called shift-sum procedure). A filter is not suitable because the waveform is a complex, multi-peaked function. To reduce noise and ensure the waveform is properly populated, the average period is calculated over a time interval (e.g., 5 minutes). If the standard deviation is too high, the waveform is not calculated because the period is changing which indicates the patient's vital signs are shifting. If the average period remains similar, each period is transformed according to sin (w(t−nT)), where n is the period number and T is the average period. Using this procedure, all waveforms nearly coincide and a waveform with a large sample set and low uncertainty may be obtained.

In adapting this procedure to derivation of pulse shape and energy of the heart, the pulse and its waveform may be extracted from two signals, the spatial variation of the pulse and the intensity (temperature) variation of the pulse. By examining the important features of the pulse waveform this procedure can calculate the periodicity using the systolic peak. The upstroke and decline then are used as inputs to the learning model for the blood pressure. The shape and intensity of the pulse are used to approximate the variations of pressure throughout the waveform. An individual waveform, which may be under 1 second and may be sampled, e.g., 15 times, generally does not neatly define the shape of the pulse from which blood pressure may be derived. The above-described shift-sum procedure addresses this problem. In employing visual data derived from thermal imaging for modeling blood pressure, temperature measurements can provide results superior to spatial measurements. Temperature measurements typically show reduced sensor noise.

Disclosed systems and methods can monitor physical characteristics of a sleeping subject 120 associated with REM sleep. REM sleep, the stage of sleep associated with dreaming, is very different physiologically from the other stages of sleep. Five stages of sleep include:

Stage 1: The first stage of sleep is the lightest stage of sleep, or transition phase. If a subject were to wake up naturally, without alarm, stage 1 sleep would be the last stage before fully waking up. Stage 1 sleep allows the individual's body to slow down and muscles to relax.

Stage 2: The second stage of sleep is still considered light sleep. Brain activity starts to slow down, as well as your heart rate, heart rate variability (HRV), and breathing. Body temperature falls a little and the individual begins to reach a state of total relaxation.

Stage 3: The third stage sleep is the start of deep sleep, also known as slow wave sleep. Muscles relax, temperature, heart rate, HRV, breathing rate and blood pressure drop.

Stage 4: During this fourth stage a person may experience deepest sleep of the night. The brain only shows delta-wave (slow wave) activity. P Temperature, heart rate, HRV, breathing rate and blood pressure drop further.

Stage 5: This is the stage of sleep in which individuals dream. It is also referred to as "active sleep," rapid eye movements (REM) sleep, or paradoxical sleep.

Typically, the skeletal muscles are atonic or without movement during REM sleep. REM atonia, an almost complete paralysis of the body, is effected through the inhibition of motor neurons. Some localized twitching and reflexes still can occur. Lack of REM atonia causes REM behavior disorder. With REM sleep behavior disorder (RBD), the paralysis that normally occurs during REM sleep is incomplete or absent, allowing the individual to "act out" his or her dreams. RBD is often characterized by the acting out of dreams that are vivid, intense, and violent. Dream-enacting behaviors can include talking, yelling, punching, kicking, sitting, jumping from bed, arm flailing, and grabbing. An acute form may occur during withdrawal from alcohol or sedative-hypnotic drugs Breathing is more erratic and irregular during REM sleep. Heart rate often increases. Systems and methods of the disclosure may analyze these and other characteristics in monitoring sleep, e.g., to measure REM sleep and monitor movements of a resting body. A larger set of metrics that may be employed in sleep metrology include core temperature, heart rate, HRV, breathing rate, respiration rate, thermal sensing of REM, audio correlations with breathing rate and spectral analysis of breathing ailments, and visual monitoring of RBD movements. In a use case, this data is employed in monitoring and characterizing any RBD. This ensemble of metrics can be used to more precise monitor and identify stages of sleep of a subject 120. Facial feature recognition (FIG. 5) may be applied to detect edges for identifying eye motion in monitoring REM sleep.

In an embodiment, the system ranks quality of sleep based on several factors. These factors may include standard deviation of the breath rate, standard deviation of the heart rate, motion of the eyes (which could indicate REM sleep), and amount of motion of the patient, e.g., as defined by velocity of tracked features. In an example, a machine learning model applying classifier/factorization machine prediction acts as a multivariate sleep quality classifier. In another example, a machine learning model applying random forest classification acts as a multivariate sleep quality classifier.

Disclosed embodiments monitor several sleep apneas. Obstructive sleep apnea (OSA) is caused by a blockage of the airway. In central sleep apnea (CSA), the airway is not blocked but the brain fails to signal the muscles to breathe. Complex sleep apnea is a combination of the two conditions. In each apnea event, the brain rouses the sleeper, usually only partially, to signal breathing to resume. In patients with severe sleep apnea, this can happen hundreds of times a night, often most intensely late in the sleep cycle during rapid-eye-movement (REM) sleep. As a result, the patient's sleep can be extremely fragmented and of poor quality. In some cases the sleeping CSA patient displays not a periodic failure to breathe but a periodic shallow breathing or under-breathing that alternates with deep over-breathing, a condition known as Cheyne-Stokes breathing. The disorder reduces oxygenation of the blood, further stressing the sleeper's health. Disclosed embodiments recognize several sleep apneas and may generate an alert/alarm if an apnea event occurs.

An additional application of thermal imaging correlates facial feature recognition of tear ducts temperature with core temperature, e.g., to determine if an individual is healthy. Skin temperature is different than core temperature but useful to monitor to check if person is in field of view and for possible health issues. Tear duct temperature is representative of core temperature. Over the course of a night, core temperature decreases slightly.

Figure 11:
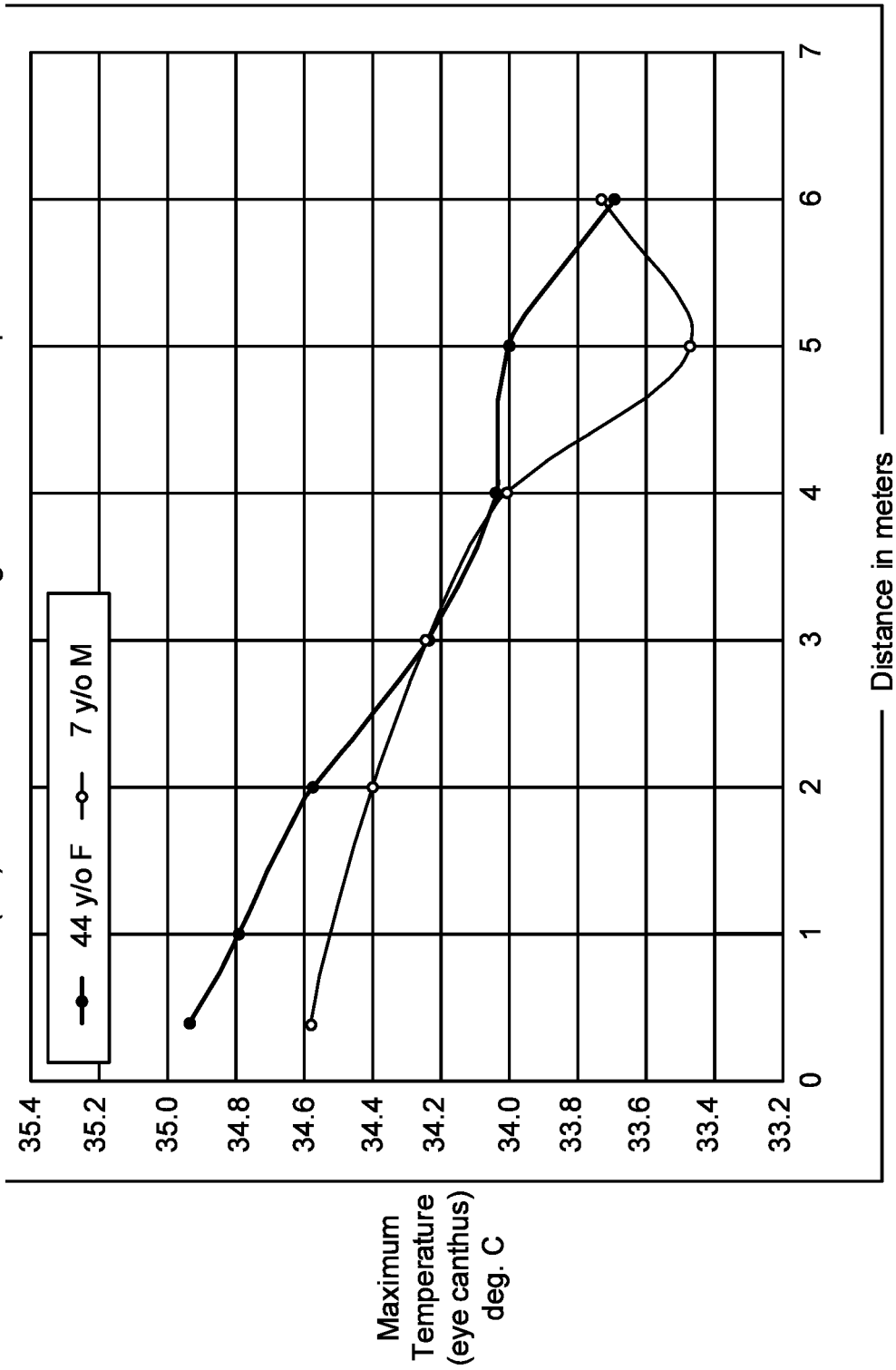
FIG. 11 is a graph of maximum facial temperature vs. camera distance, according to an embodiment.

In an embodiment, feature detection observes the tear ducts. Locations of the tear ducts may be identified using the same machine learning model that has been trained to identify other facial features (FIG. 5). This thermal imaging data may be employed to calculate core temperature. FIG. 11 is a graph of maximum facial temperature as a function of camera distance, measured for 44 year old female and 7 year old male. The imaging system estimates proximity of the thermal camera to the subject to correct core temperature readings. Based on field of view and number of pixels occupied by face, the system can estimate distance from the camera. Using this estimate, the correction reduces temperature recorded by camera for range. This calculation and predetermined relationship shown in FIG. 11 enable accurate determination of core temperature from tear duct temperature observations. In an example, distance is measured using FLIR® Research Studio software. FLIR is a registered trademark of Teledyne FLIR, LLC, Wilsonville OR.

Figure 12:
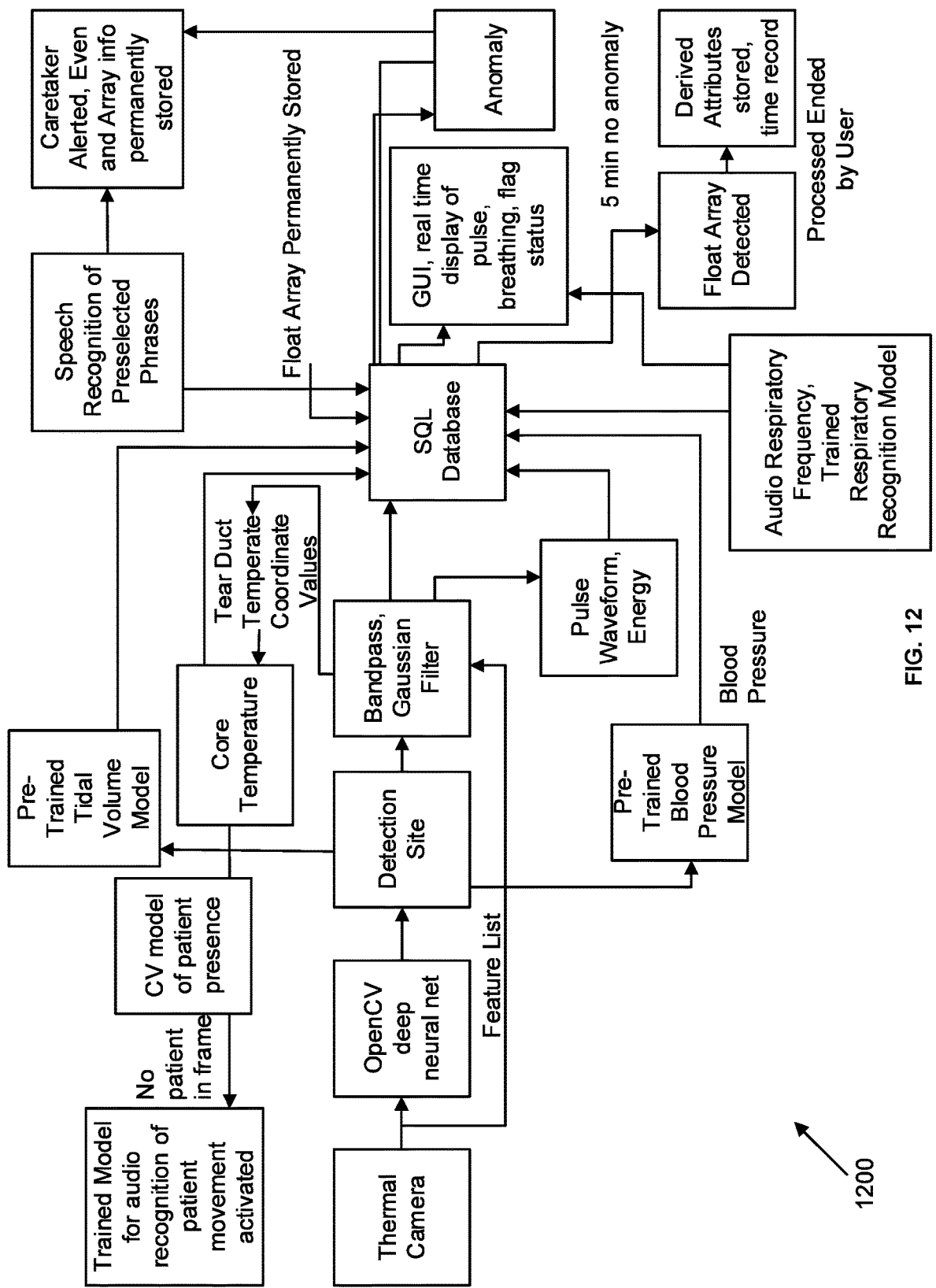
FIG. 12 is a schematic block diagram of a general health monitoring architecture, according to an embodiment.

FIG. 12 is a schematic block diagram of a general health monitoring architecture 1100. Key functions include:
- management of SQL data storage via ongoing deletion of thermal image float arrays, and storage and data logging of derived attributes;
- real-time anomaly detection, generation of flags, and display of alerts/alarms;
- real-time display of pulse status, breathing status, and flags status;
- thermal imaging monitoring of patient presence; other patient monitoring modalities including audio recognition may be activated by "no patient present" flag resulting from CV monitoring;
- audio respiratory recognition model;
- derivation of pulse waveform and energy from acquired thermal images;
- pre-trained blood pressure model and pre-trained tidal volume model, each of which inputs CV data derived from digitized thermal images; and
- core temperature model derived from tear duct coordinate values.

Foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc., are not intended to limit the order of the steps; these words are simply used to guide the reader through the description of the methods. Although process flow diagrams may describe the operations as addition, the order of the operations may be rearranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc., may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage, or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A monitoring system, comprising:
   a visual sensor configured to monitor one or more cardiovascular features of a human subject selected from carotid arteries in a neck, carotid arteries in a temple, arteries in an arm, and arteries in a hand, wherein the visual sensor comprises a thermal camera configured to output thermal image signals representing the one or more cardiovascular features; and
   a processor communicatively coupled to the visual sensor and a non-transitory computer-readable medium containing instructions that when executed by the processor causes the processor to perform operations comprising:
      in response to receiving the thermal image signals from the visual sensor, generate higher order data derived from the thermal image signals, wherein the higher order data comprises thermal imaging spatial data and thermal imaging temperature data,
         wherein the thermal imaging spatial data defines a feature set of pixels for each of the one or more cardiovascular features represented by the received thermal image signals,
         wherein the thermal imaging temperature data comprises temperature gradient data including a maximum thermal point within each feature set of pixels;
      execute a supervised machine learning model configured to input the higher order data to determine a blood pressure data for the human subject, wherein the supervised machine learning model has been trained to fit data representative of systolic pressure characteristics and data representative of diastolic pressure characteristics; and
      in an event the blood pressure data for the human subject indicates a predetermined cardiovascular event, display an alert by a user device coupled to the processor.

2. The monitoring system of claim 1, further comprising performing computer vision feature recognition to identify the one or more cardiovascular features of the human subject, wherein each feature set of pixels comprises a square area of pixels.

3. The monitoring system of claim 1, wherein the higher order data applies a weighting function to the temperature gradient data that assigns highest weight to the maximum thermal point within each feature set of pixels.

4. The monitoring system of claim 1, wherein the higher order data comprises a two-dimensional (2D) array that varies in time, wherein generate higher order data comprises performing principal component analysis to extract information from the 2D array that varies in time.

5. The monitoring system of claim 4, wherein the thermal image signals comprise dynamic thermal images including a plurality of frames, wherein the generate step analyzes each frame of the dynamic thermal images to derive a 2D array for each frame.

6. The monitoring system of claim 4, wherein the generate step analyzes the 2D array that varies in time to derive a rate signal in a frequency domain, wherein the rate signal represents one or more of pulse rate, pulse rate variability (PRV), heart rate, and heart rate variability (HRV).

7. The monitoring system of claim 1, wherein the higher order data includes a pulse waveform signal representing a waveform of a blood pressure, wherein the supervised machine learning model receives an input of the pulse waveform signal, wherein the supervised machine learning model is configured to determine a systolic blood pressure value and a diastolic blood pressure value associated with the waveform of the blood pressure.

8. The monitoring system of claim 1, wherein the supervised machine learning model has been trained by inputting a blood pressure profile and a secondary data source into a factorization machine for systolic pressure and a factorization machine for diastolic pressure, wherein the secondary data source comprises ground truth data obtained from intra-arterial measurement of blood pressure.

9. The monitoring system of claim 8, wherein the supervised machine learning model training derives the blood pressure profile by inputting an array of thermal imaging data and a feature coordinate list to determine pulse data in a time domain.

10. The monitoring system of claim 1, wherein the systolic pressure characteristics comprise one or more of systolic pressure, systolic upstroke, systolic decline, dicrotic notch, and diastolic runoff; and wherein the diastolic pressure characteristics comprise diastolic end pressure.

11. The monitoring system of claim 1, wherein the predetermined cardiovascular event indicates sudden hemodynamic instability of the human subject.

12. The monitoring system of claim 1, wherein the visual sensor is further configured to monitor one or more cardiopulmonary features of the human subject selected from a chest, a throat, a mouth, one or more nostrils, one or more eyes, or one or more tear ducts, wherein the thermal camera is further configured to output the thermal image signals representing the one or more cardiopulmonary features.

13. The monitoring system of claim 12, wherein the thermal imaging temperature data comprises at least one corrected tear duct coordinate temperature value of the human subject, wherein the supervised machine learning model comprises a core temperature model derived from at least one tear duct coordinate value of the human subject, wherein the processor is further configured to determine a health indicator of the human subject and, responsive to the health indicator indicating a predetermined first event, display a second alert by the user device.

14. The monitoring system of claim 12, wherein the thermal imaging temperature data comprises at least one of a chest, a throat, a mouth, or one or more nostril temperature values of the human subject, wherein the supervised machine learning model comprises a pulmonary model derived from at least one of a chest, a throat, a mouth, or one or more nostril coordinate values of the human subject, wherein the processor is further configured to apply an audio recognition model to an audio data received from an audio sensor to determine a second pulmonary health indicator and, responsive to the pulmonary model indicating a predetermined event, display a third alert by the user device.

15. A method, comprising:
responsive to receiving a thermal image signal from a visual sensor, generating, by a processor coupled to the visual sensor, a higher order data derived from the thermal image signal, wherein the higher order data comprises thermal imaging spatial data and thermal imaging temperature data of a human subject,
wherein the thermal imaging spatial data defines a feature set of pixels for each of one or more cardiovascular features represented by the received thermal image signal,
wherein the thermal imaging temperature data comprises temperature gradient data including a maximum thermal point within each feature set of pixels;
executing, by the processor, a supervised machine learning model configured to input the higher order data to determine a blood pressure data for the human subject, wherein the supervised machine learning model has been trained to fit data representative of systolic pressure characteristics and data representative of diastolic pressure characteristics; and
in an event the blood pressure data for the human subject indicates a predetermined cardiovascular event, transmitting, by the processor, instructions to a user device to display an alert.

16. The method of claim 15, further comprising performing, by the processor, computer vision feature recognition to identify the one or more cardiovascular features of the human subject, wherein each feature set of pixels comprises a square area of pixels.

17. The method of claim 15, further comprising:
monitoring, by the processor, one or more cardiopulmonary features of the human subject selected from a chest, a throat, a mouth, one or more nostrils, one or more eyes, or one or more tear ducts; and
outputting, by the processor, the thermal image signal representing the one or more cardiopulmonary features.

18. The method of claim 17, wherein the thermal imaging temperature data comprises at least one corrected tear duct coordinate temperature value of the human subject, wherein the supervised machine learning model comprises a core temperature model derived from at least one tear duct coordinate value of the human subject, the method further comprising determining, by the processor, a health indicator of the human subject and, responsive to the health indicator indicating a predetermined first event, transmitting, by the processor, instructions to the user device to display a second alert.

19. The method of claim 17, wherein the thermal imaging temperature data comprises at least one of a chest, a throat, a mouth, or one or more nostril temperature values of the human subject, wherein the supervised machine learning model comprises a pulmonary model derived from at least one of a chest, a throat, a mouth, or one or more nostril coordinate values of the human subject, the method further comprising applying, by the processor, an audio recognition model to an audio data received from an audio sensor to determine a second pulmonary health indicator and, responsive to the pulmonary model indicating a predetermined event, transmitting, by the processor, instructions to the user device to display a third alert.

* * * * *